(12) United States Patent
Rieth

(10) Patent No.: US 7,892,179 B2
(45) Date of Patent: Feb. 22, 2011

(54) APPARATUS, METHOD AND SYSTEM FOR DETERMINING A PHYSIOLOGICAL CONDITION WITHIN A MAMMAL

(75) Inventor: Harry T. Rieth, Doylestown, PA (US)

(73) Assignee: PH Diagnostics, Inc.

( * ) Notice: Subject to any disclaimer, the term of this patent is extended or adjusted under 35 U.S.C. 154(b) by 0 days.

(21) Appl. No.: 12/778,406

(22) Filed: May 12, 2010

(65) Prior Publication Data

US 2010/0217101 A1    Aug. 26, 2010

Related U.S. Application Data

(63) Continuation of application No. 12/536,052, filed on Aug. 5, 2009.

(60) Provisional application No. 61/231,076, filed on Aug. 4, 2009, provisional application No. 61/086,403, filed on Aug. 5, 2008.

(51) Int. Cl.
| | |
|---|---|
| A61B 10/00 | (2006.01) |
| A61B 5/103 | (2006.01) |
| A61B 5/117 | (2006.01) |
| A61B 5/05 | (2006.01) |
| A61B 5/00 | (2006.01) |
| B65D 81/00 | (2006.01) |

(52) U.S. Cl. ............... 600/551; 600/345; 600/361; 600/549; 600/587; 600/591; 600/573; 600/366

(58) Field of Classification Search ........... 600/551, 600/300, 301, 304, 372, 373, 376, 546, 547, 600/549, 587, 591, 38, 309, 345, 348, 361, 600/3, 119, 366, 367, 397, 573, 575; 374/100, 374/101, 102, 103, 158, 163, 208, 209, 210; 204/228.6, 228.1, 193, 416, 417, 433; 324/438, 324/425; 205/787.5; 257/253, 414; 607/138; 73/73

See application file for complete search history.

(56) References Cited

U.S. PATENT DOCUMENTS

| | | | |
|---|---|---|---|
| 4,473,458 A | 9/1984 | Schwartz et al. | |
| 4,478,222 A | 10/1984 | Koning et al. | |
| 5,209,238 A * | 5/1993 | Sundhar | 600/551 |
| 5,916,173 A * | 6/1999 | Kirsner | 600/551 |
| 6,080,118 A * | 6/2000 | Blythe | 600/591 |
| 6,117,292 A | 9/2000 | Ahmad | |
| 6,364,844 B1 | 4/2002 | Regas et al. | |
| 6,447,448 B1 | 9/2002 | Ishikawa | |
| 6,623,698 B2 * | 9/2003 | Kuo | 422/68.1 |
| D491,274 S * | 6/2004 | Dubniczki et al. | D24/223 |
| D548,359 S * | 8/2007 | Illein et al. | D24/223 |
| 7,577,476 B2 * | 8/2009 | Hochman et al. | 600/546 |
| 7,736,320 B2 | 6/2010 | Tsukashima et al. | |
| 2003/0100819 A1 | 5/2003 | Newman et al. | |
| 2007/0025415 A1 | 2/2007 | Chen | |

(Continued)

*Primary Examiner*—Jeffrey G Hoekstra
(74) *Attorney, Agent, or Firm*—The Belles Group, P.C.

(57) ABSTRACT

A system, method and apparatus for determining a physiological condition within a mammal based on pH and/or temperature measurements. The invention is for determining vaginal health and/or fertility status in a female mammal based on pH and/or temperature measurements of vaginal and/or cervical fluids or tissue. The invention is suited for taking either in vivo or external measurements. In one aspect, the invention is an apparatus comprising an elongated probe portion and a handle portion. In one embodiment, the circuitry of the apparatus is strategically split between the probe portion and the handle portion to facilitate a plug-and-play type of device. In another embodiment, an elongated probe is provided that has a hermetically sealed internal cavity that houses the circuitry while leaving the temperature sensor and the pH sensor exposed for direct contact with the desired biological fluid. In a further embodiment, an ISFET is used as the pH sensor.

18 Claims, 16 Drawing Sheets

U.S. PATENT DOCUMENTS

2007/0032747 A1 2/2007 Hashimshony et al.
2007/0138027 A1 6/2007 Dinsmoor et al.
2008/0071190 A1 3/2008 Gorodeski et al.
2009/0274192 A1 11/2009 Tseng

* cited by examiner

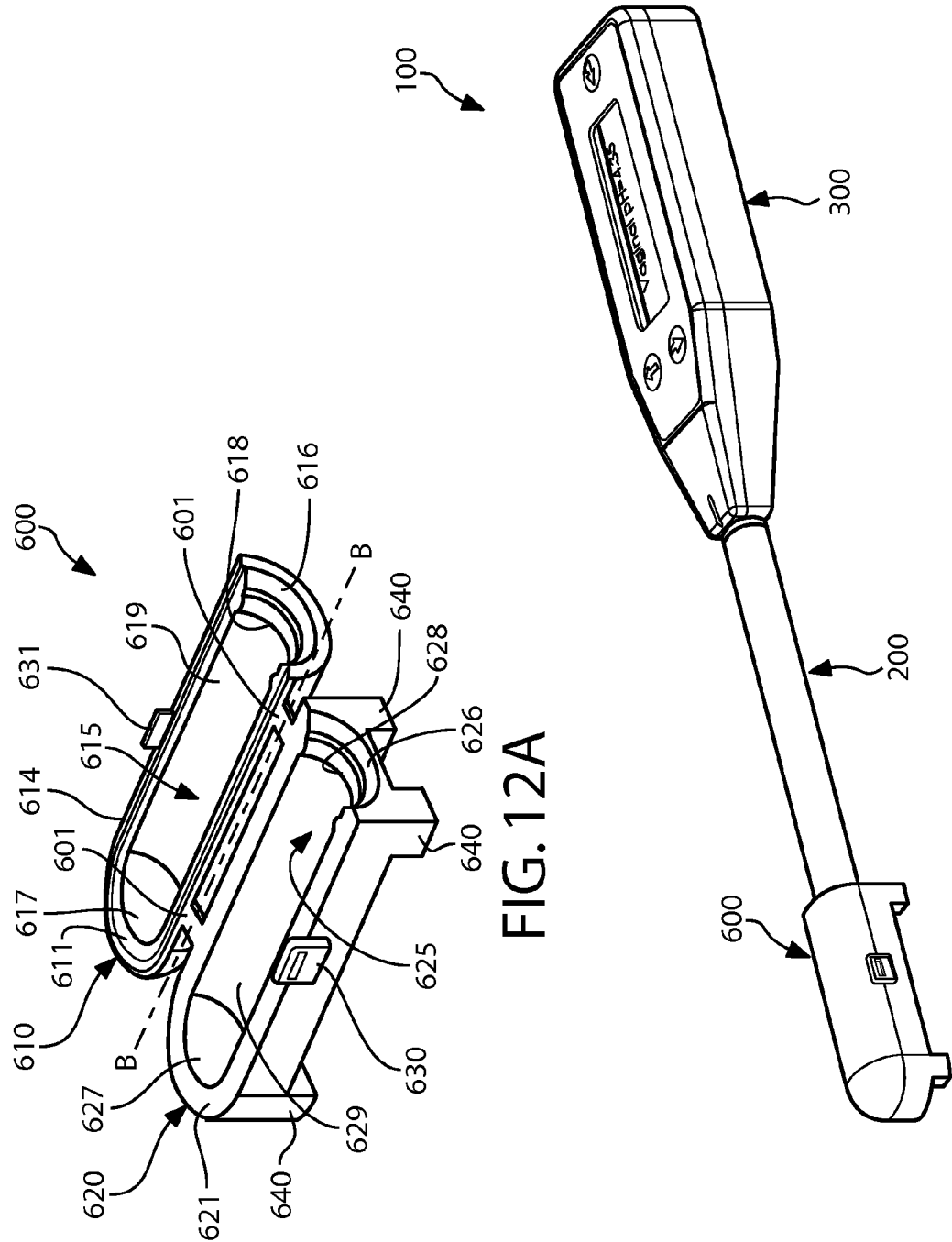

APPARATUS, METHOD AND SYSTEM FOR DETERMINING A PHYSIOLOGICAL CONDITION WITHIN A MAMMAL

CROSS-REFERENCE TO RELATED PATENT APPLICATIONS

The present application is a continuation of U.S. patent application Ser. No. 12/536,052, filed Aug. 5, 2009, which in turn claims the benefit of U.S. Provisional Patent Application Ser. No. 61/231,076, filed Aug. 4, 2009 and U.S. Provisional Patent Application Ser. No. 61/086,403, filed Aug. 5, 2008, the entireties of which are hereby incorporated by reference.

FIELD OF THE INVENTION

The present invention relates generally to the field of determining a physiological condition within a mammal, and specifically to apparatus, methods and systems of determining a physiological condition within a mammal based on pH measurements of biological fluids taken either in vivo or externally, such as ovulation, vaginal and/or cervical health, and other physiological conditions.

The device is particularly suited for insertion into the vagina but allows for easy pH measurement of small samples of various other bodily fluids (urine, saliva, blood) external of the body. The device shown is designed for female end user self testing but can also be a valuable aid in physicians offices and clinical labs. The invention can be used for various mammals, including human and veterinary applications.

BACKGROUND OF THE INVENTION pH is a measure of the acidity of alkalinity of a solution or substance. Solutions with a pH less than seven are considered acidic, while those with a pH greater than seven are considered basic or alkaline. A pH level of 7.0 is considered neutral. When a pH level is 7.0, it is defined as 'neutral' because at this pH the concentration of $H_3O^+$ equals the concentration of $OH^-$ in pure water. The pH value is a measure of the activity of hydrogen ions in the solution. The pH scale is typically between 1 and 14 with 1 being the most acidic and 14 the most alkaline. The pH scale is an inverse logarithmic representation of hydrogen proton concentration. Therefore a value change of 1 pH unit represents a factor of 10 increase or decrease.

The vagina is the muscular canal extending from the vaginal opening to the cervix and consists of three layers of tissue. The mucosa is the surface layer and consists of mucus membranes. The next layer of tissue is a layer of muscle concentrated mostly around the outer third of the vagina. The third layer is the innermost layer and consists of fibrous tissue.

The vagina contains folds or wrinkles rather than a smooth surface. It is usually about 3 to 5 inches in length and its walls are lined with a mucus membrane. The vagina includes numerous tiny glands that generate vaginal secretions/fluids. The vaginal walls are continually producing secretions/fluids necessary to provide lubrication, to cleanse the vagina and to maintain the proper acidity to prevent infection. The vagina tends to be fairly acidic usually in the range of 3.5 to 4.5 pH. The walls of the vagina are normally in contact with each other, which is contrary to most anatomical illustrations. When something enters the vagina, its walls separate to make room for the object. Because of its muscular tissue, the vagina has the ability to expand and contract adjusting to fit snugly around the object inserted.

Accurate monitoring of vaginal pH is an important part of in the diagnosis of vaginal infections such as Bacterial Vaginitis (BV). The normal vaginal pH in reproductive age women is usually 3.5 to 4.5. A value greater the 4.5 can indicate a variety of vaginal infections which are usually accompanied by unusual discharge, itching, burning and irritation. The three diseases most frequently associated with vaginal discharge are BV, trichomoniasis (caused by a sexually transmitted infectious parasite), and candidiasis (usually caused by *Candida albicans*).

Bacterial vaginosis (BV) is the most common cause of vaginal infection. BV is caused by an imbalance of naturally occurring bacterial flora. To control bacterial growth, the vagina is normally slightly acidic with a pH of 3.5-4.5. A pH greater than 4.5 is considered alkaline and is suggestive of bacterial vaginosis.

Candidiasis, also known as a "yeast infection" or VVC, is a common fungal infection that occurs when there is overgrowth of the fungus called *Candida*. *Candida* is always present in the body in small amounts, however when an imbalance occurs, such as when the normal acidity of the vagina changes or when hormonal balance changes, *Candida* can multiply. When that happens, symptoms of candidiasis appear.

Trichomoniasis, sometimes referred to as "trich," is a common cause of vaginitis. Trichomoniasis is primarily an infection of the urogenital tract with the most common site of infection the vagina or urethra in women. With a trichomonas infection, the vagina is likely to be more alkaline than normal. An estimated five million cases of trichomoniasis occur each year in the United States. Men also can contract trichomoniasis however do not often have signs or symptoms. Some men may temporarily have an irritation inside the penis, mild discharge, or slight burning after urination or ejaculation.

According to the Centers for Disease Control (CDC), there are some serious risks from BV such as;

An increase in a woman's susceptibility to HIV infection if she is exposed to HIV virus.

An increase in the chances that an IHV-infected woman can pass HIV to her sex partner.

An increase in a woman's susceptibility to other STDs, such as herpes simples virus (HSV) Chlamydia and gonorrhea.

An increase in the development of an infection following surgical procedures such as a hysterectomy or an abortion.

During pregnancy, an increase in adverse pregnancy outcomes has been detected, including premature rupture of the membranes, preterm labor, preterm birth, intraamniotic infection, and postpartum endometritis.

The results of several investigations indicate that treatment of pregnant women with BV who are at high risk for preterm delivery (i.e., those who previously delivered a premature infant) might reduce the risk for prematurity. Monitoring of pH level during pregnancy is an important criterion in reducing the incidences of Preterm labor and birth. Studies have shown that bacterial vaginosis was associated with the preterm delivery of low-birth-weight infants independently of other recognized risk factors. Reduction in the instances of pre-mature birth improves the health of the newborn and significantly reduces the cost of care.

Oral clindamycin prevents spontaneous preterm birth and mid trimester miscarriage in pregnant women with bacterial vaginosis. Based on estimates from the CDC, the number of pregnant women in the United States alone that are annually infected with BV is 1,080,000 and Trichomoniasis is 124,000.

Untreated bacterial vaginosis is a risk factor for post abortion pelvic inflammatory disease (PID). Studies have shown that preabortal screening and subsequent treatment of those who test clinically positive does lower the incidence of postabortion PID.

BV can be diagnosed by the use of clinical criteria or Gram stain. In clinical practice BV is diagnosed using the Amsel criteria. Clinical criteria require typically three of the following symptoms or signs:

homogeneous, thin, white discharge that smoothly coats the vaginal walls;
presence of clue cells on microscopic examination;
pH of vaginal fluid>4.5; and
a fishy odor of vaginal discharge before or after addition of 10% KOH (i.e., the whiff test).

Current methods of monitoring vaginal pH include various methods of checking pH paper type products. The accuracy of these products are generally in the range of 0.3 pH to 0.5 pH. They generally require the user to subjectively compare color in order to determine the pH value and are subject to inaccuracies. Inaccuracies can be due to lighting conditions or the ability of the user to accurately compare color. Manual recording of the subjective readings is required.

The cervix is the lower portion of the uterus and forms the neck of the uterus. The cervix joins with the top end of the vagina and the uterine cavity. The cervix protrudes into the vagina and this area is called the ectocervix. Typically the ectocervix is about 2.5 to 3 cm in diameter and has an elliptical surface. The ectocervix is also called the external os. The size and shape of the external os can vary widely depending on the age of the woman or if she has given vaginal birth. The passage way between the external os and the uterus is referred to as the endocervical canal. The endocervical canal terminates at the internal os which is the opening of the cervix inside the uterine cavity. The cervical canal of the uterus is covered by a thin layer of mucus. Pockets within the lining of the cervix function to produce cervical fluid.

Studies by George I. Gorodeski et al, such as those disclosed in U.S. Patent Application US/2008/0071190 published Mar. 20, 2008, show that cervical pH changes dramatically during the ovulation cycle while the vaginal pH remains relatively constant. The in-vivo vaginal and cervical pH values recorded were measured in Gorodeski by attaching a strip of pHydrion paper at the tip of uterine forceps. In addition, another more complicated clinical lab test was preformed by measuring cell cultures of the human Ecto-cervical Epithelial cells and human Endocervical cells. These tissue samples were collected and then analyzed and measured using an elaborate clinical procedure. Using these techniques, it was shown that the pH of the ectocervix changes as much as 2 pH during the ovulation cycle with the peak occurring during days 11-14 Of the cycle (ovulation period). During the same periods the vaginal readings remained relatively constant.

Studies have also shown that monitoring of vaginal pH can be a good indicator of menopause in women who are without vaginitis and are not receiving estrogen therapy. A pH reading greater than 4.5 could indicate menopause and the need for estrogen therapy. Low levels of estrogen can cause elevated pH levels in the area of 6.0 or higher. The sensitivity of FSH blood work was no different than vaginal pH in the diagnosis of menopause. Estrogen causes deposition of glycogen in mature epithelial cells, which is then converted by bacterial enzymes to glucose. The glucose is anaerobically fermented to lactic acid, which gives the vagina a pH of 3.5 to 4.5.

Further studies have shown that an important function of the vaginal and cervical epithelial cells is to regulate the pH of the lumen of the lower genital tract. During premenopausal years vaginal luminal pH ranges between 4.5 and 6.0 with mild alkalinization to about 6.5 before ovulation. Lack of estrogen, such as after menopause, is associate with alkalinization to about 6.5-7.0, whereas replacement with estrogen can acidify the luminal vaginal pH to about 5.5.

On a related note, there are times when urine pH can indicate serious health issues. For example, a very high (alkaline) urine pH could be caused by kidney failure or a urinary tract infection. A very low (acidic) urine pH could be the result of lung disease, complications of diabetes, starvation, or diarrhea. The glomerular filtrate of blood is usually acidified by the kidneys from a pH of approximately 7.4 to a pH of about 6 in the urine. Depending on the person's acid-base status, the pH of urine may range from 4.5 to 8. The kidneys maintain normal acid-base balance primarily through the reabsorption of sodium and the tubular secretion of hydrogen and ammonium ions. Urine becomes increasingly acidic as the amount of sodium and excess acid retained by the body increases. Alkaline urine, usually containing bicarbonate-carbonic acid buffer, is normally excreted when there is an excess of base or alkali in the body. Secretion of acidic or alkaline urine by the kidneys is one of the most important mechanisms the body uses to maintain a constant body pH.

A highly acidic urine pH occurs in:
Acidosis
Uncontrolled diabetes
Diarrhea
Starvation and dehydration
Respiratory diseases in which carbon dioxide retention occurs and acidosis develops
A highly alkaline urine occurs in:
Urinary tract obstruction
Pyloric obstruction
Salicylate intoxication
Renal tubular acidosis
Chronic renal failure
Respiratory diseases that involve hyperventilation (blowing off carbon dioxide and the development of alkalosis)

Urine pH is often used to monitor a person's diet. In people who are not vegetarians, the of urine tends to be acidic. A diet rich in citrus fruits, legumes, and vegetables raises the pH and produces urine that is more alkaline. Generally an accurate measurement of urinary pH can be done only on a freshly voided specimen. If urine pH is to be useful, it is necessary to use pH information in comparison with other diagnostic information.

SUMMARY OF THE INVENTION

It is therefore an object of the present invention to provide an apparatus, system and method for determining one or more physiological conditions within a mammal based on pH measurements, including without limitation one or more of the physiological conditions discussed above.

Another object of the present invention is to provide an apparatus, system and method for measuring pH and temperature of a biological fluid.

Yet another object of the present invention is to provide an apparatus, system and method for determining a physiological condition within a mammal based on either in vivo or external measurements of biological fluids.

Still another object of the present invention is to provide an apparatus, system and method for determining a physiological condition within a mammal that requires minimal calibration.

A further object of the present invention is to provide an apparatus, system and method for determining a physiological condition within a mammal that utilizes a replaceable "plug-and-play type" of probe.

A yet further object of the present invention is to provide an apparatus, system and method for determining a physiological condition within a mammal that utilizes a dark environment for calibration.

A still further object of the present invention is to provide an apparatus, system and method for determining a physiological condition within a mammal that utilizes an ion-sensitive field effect transistor (ISFET) for measuring pH.

An even further object of the present invention is to provide an apparatus, system and method for determining a physiological condition within a mammal wherein the processing and logic circuitry is maintained in a handle and a minimal amount of circuitry is maintained in a replaceable probe.

Another object of the present invention is to provide an apparatus, system and method for determining the fertility status of a female mammal.

Yet another object of the present invention is to provide an apparatus, system and method for predicting ovulation in a female mammal based on current and stored pH and/or temperature measurements.

These and other objects are met by the present invention which, in one aspect, is an apparatus for measuring a physiological condition within a mammal comprising: a probe for insertion into a body lumen of the mammal, the probe comprising: an elongated tubular housing having a first internal cavity; a first circuit board located within the first internal cavity; a pH sensor for measuring pH within the body lumen located at a distal portion of the elongated tubular housing, the sensor generating a pH signal indicative of the measured pH and operably coupled to the first circuit board; a memory device storing parametric data unique to the pH sensor, the memory device located within the first internal cavity and operably coupled to the first circuit board; and a first interface connector located at a proximal portion of the elongated tubular housing and operably coupled to the first circuit board; a handle for manipulating the probe, the handle comprising: a second housing having a second internal cavity; a second circuit board located within the second internal cavity; a microprocessor for processing the pH signal and generating an output signal based on the processing of the pH signal, the microprocessor located within the second internal cavity and operably coupled to the second circuit board; a display device on the second housing for displaying the output signal generated by the microprocessor and operably coupled to the second circuit board; and a second interface connector located at the second housing and operably coupled to the second circuit board; the probe connected to the handle in a manner that allows the probe and the handle to be repetitively engaged and disengaged from each other; and wherein when the probe is connected to the handle, the first and second interface connectors are in electrical connection so that the microprocessor can retrieve the parametric data from the memory device of the probe and receive the pH signal.

In another aspect, the invention is an apparatus for measuring a physiological condition within a mammal comprising: an elongated housing extending along a longitudinal axis from a proximal end to a distal end, the housing having an internal cavity; a transverse wall extending along the longitudinal axis that separates the internal cavity into a first chamber and a second chamber, the first and second chambers isolated from one another and extending in an axially adjacent manner along the longitudinal axis; a par-cylindrical cutout in the elongated housing forming an open end of the first chamber and exposing a portion of the transverse wall; a pH sensor for measuring pH within a body lumen or the mammal and a temperature sensor for measuring temperature within the body lumen of the mammal, the pH sensor and the temperature sensor operably coupled to a first circuit board and located on the exposed portion of the transverse wall; a par-cylindrical cover having a well for collecting biological fluids, the well defined by an annular wall and a floor, and first and second openings forming first and second passageways through the floor of the well respectively; and the par-cylindrical cover secured to the elongated housing so that the pH sensor is exposed via the first opening and the temperature sensor is exposed via the second opening, the par-cylindrical cover covering the par-cylindrical cutout so as to hermetically seal the open end of the first chamber.

In a further aspect, the invention is an apparatus for measuring a physiological condition within a mammal comprising: an elongated probe for insertion into a body lumen of the mammal, the probe comprising a first circuit board operably coupling an ion-sensitive field effect transistor (ISFET) for measuring pH within the body lumen and generating a pH signal indicative of the measured pH, a temperature sensor for measuring temperature within the body lumen and generating a temperature signal indicative of the measured temperature, a diaphragm in contact with an electrolyte solution buffered at a known pH, a memory device storing ISFET slope data at both ambient temperature and normal body temperature for the ISFET, and a first interface connector, wherein the ISFET, temperature sensor and diaphragm are located at a distal portion of the probe and the first interface connector is located at a proximal portion of the probe; a handle for manipulating the probe, the handle comprising a second circuit board operably coupling a microprocessor for receiving the pH and temperature signals and generating an output signal based on the processing of the pH and temperature signals and the ISFET slope data, a display device for displaying the output signal generated by the microprocessor, and a second interface connector; the probe connected to the handle in a manner that allows the probe and the handle to be repetitively engaged and disengaged from each other; and wherein when the probe is connected to the handle, the first and second interface connectors are in electrical connection so that the microprocessor can retrieve the ISFET slope data from the memory device of the probe and receive the pH and temperature signals.

BRIEF DESCRIPTION OF THE DRAWINGS

FIG. 12A is a perspective view of a removable cap according to one embodiment of the present invention, the removable cap being in an open position.

FIG. 12B is a perspective view of a vaginal health system according to one embodiment of the present invention including the vaginal health apparatus of FIG. 1 and the removable cap of FIG. 12A.

DETAILED DESCRIPTION OF THE INVENTION

Figure 1:
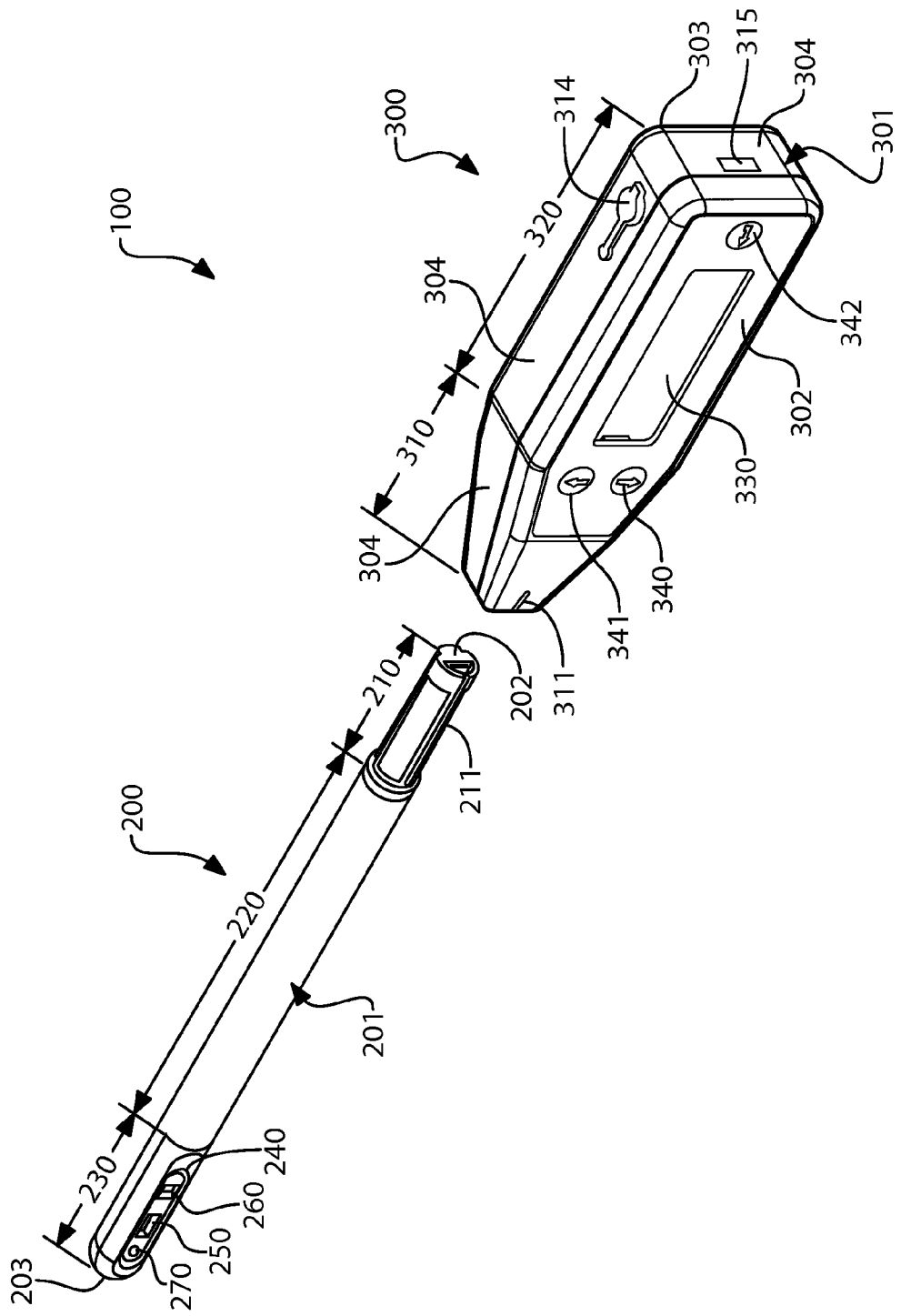
FIG. 1 is an isometric view of a vaginal health apparatus according to an embodiment of the present invention, wherein the probe has been disassembled from the handle.

One or more embodiments of the present invention will be discussed in this section with reference to FIGS. 1-17. The embodiments illustrated herein are not intended to be exclusive or to limit the invention to the precise form or application disclosed. The embodiments are chosen and described merely to explain one or more desired embodiment of the structure, use and/or application of the invention. While the invention is specifically described below as a "vaginal health device," the invention is not limited to this application or to the exact structure exemplified. The present invention can be used to determine any physiological condition of a mammal that can be determined by pH and/or temperature values and/or variations thereof over a period of time. The invention can be used to determine any physiological condition, such as fertility, vaginal health, oral health, gastro-intestinal health, dietary health, etc. Specific examples of physiological conditions within the scope of this invention include without limitation ovulation, menopause, acidosis, diabetes, diarrhea, starvation and dehydration, respiratory disease, urinary tract obstruction, pyloric obstruction, salicylate intoxication, renal tubular acidosis, chronic renal failure, BV, candidiasis and trichomoniasis. Moreover, the present invention can be used to measure the pH and/or temperature of biological fluids both externally and in vivo. For external measurements, the sample well allows for the accurate measurement of pH and/or temperature for bodily fluids such as saliva, urine and blood. For in vivo measurements, the invention can also take pH and/or temperature measurements in any desired body lumen, including without limitation the vagina, cervix, esophagus, mouth, nasal passages, auditory canals, digestive tract, urethra, and vascular system.

The invention is generally described in relation to the human female. However, the inventive principals can be applied in veterinary applications with a simple modification of the size (length and diameter) and/or shape of the structure to fit various mammals including dogs, cats, dairy cows and horses. As a result, veterinary applications for monitoring vaginal pH, cervical pH, oral pH or urinary pH can be accomplished for diagnosis and determination of a physiological condition in the art of veterinary medicine.

The invention allows for measurement of the pH and/or temperature of biological fluids in a private (i.e., in the home) or clinical lab environment. As will be discussed in detail below, the invention allows for easy change, updating and/or replacing of the probe of the apparatus to keep up with latest technologies in measuring pH. For example, in some embodiments of the invention, the pH sensor may be a reference FET (REFET) which could be implemented with an ISFET and a pseudo reference electrode. In such a design, the electrode wire (which is typically an Ag/AgCL coated wire) and electrolyte solution may be eliminated.

Additionally, the incorporation of the vital product data (VPD) into a memory device within the probe of the apparatus allows the probe to be easily interchanged with other logic assemblies without the need for extensive two point calibration. The incorporation of the VPD information within the probe itself simplifies user operation as key information about the probe characteristics and use are stored within the memory device of the probe itself. The logic assembly (which acts as the handle) can easily read this information in order to guide the user through proper operation, whether it is taking measurements or calibration. The ability to store and retrieve important calibration and other information within the probe make the invention a "plug-and-play" type of device.

Figure 9:
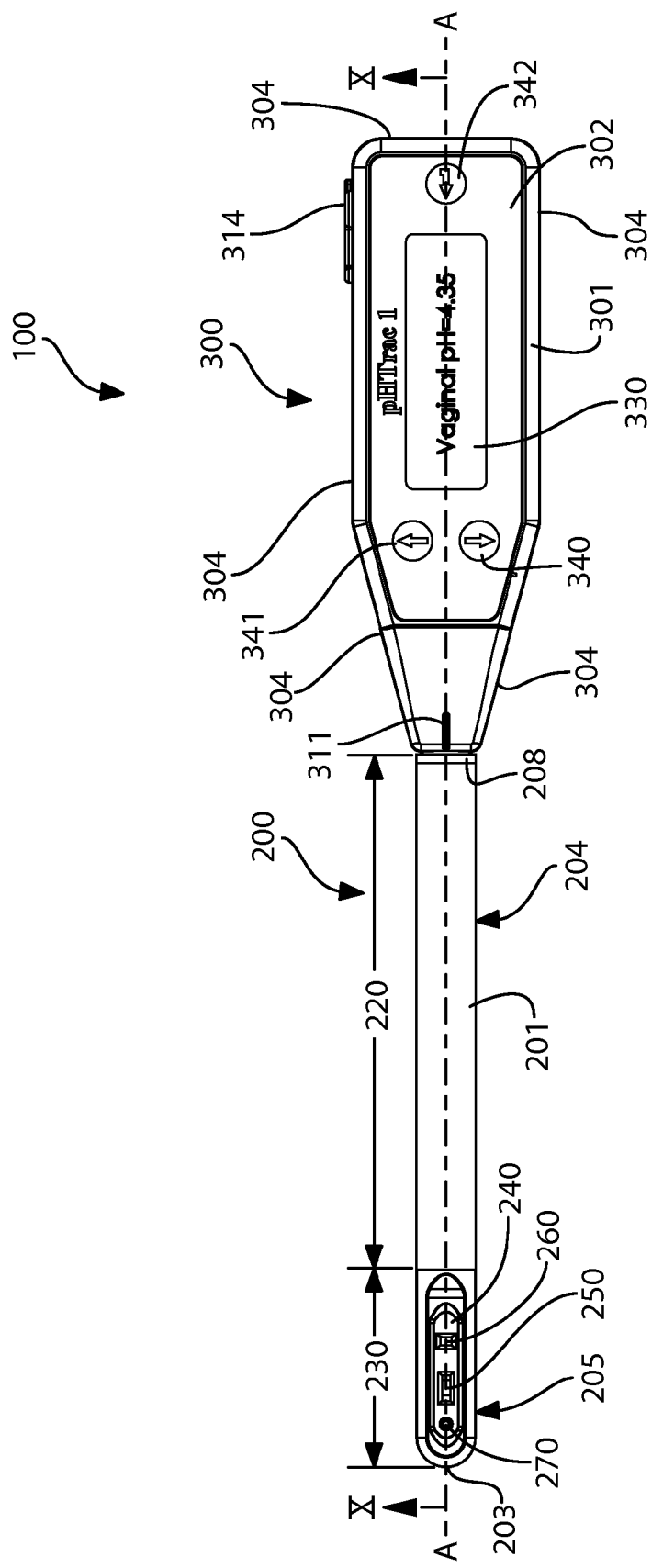
FIG. 9 is a top view of the vaginal health apparatus of FIG. 1 in an assembled state.

Referring now to FIGS. 1 and 9, a vaginal health apparatus 100 is illustrated according to one embodiment of the present invention. The vaginal health apparatus 100 generally comprises a probe component 200 (sometimes referred to as the "probe") and a handle component (sometimes referred to as the "handle). The vaginal health apparatus 100 is illustrated in FIG. 1 in a disassembled state wherein the probe 200 has been disconnected from the handle 300. In FIG. 9, the vaginal health apparatus 100 is illustrated in an assembled state wherein the probe 200 is connected to the handle 300.

Figure 4:
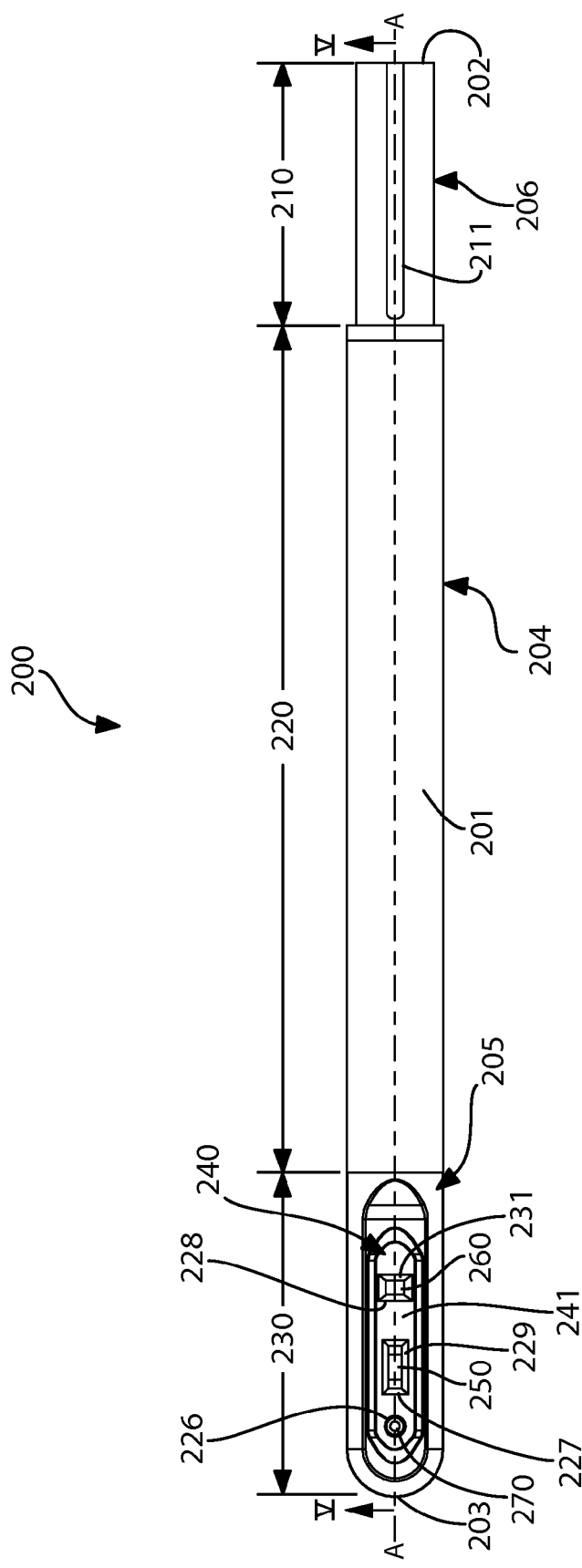
FIG. 4 is a top view of the probe of the vaginal health apparatus of FIG. 1.

The general structure and shape of the probe 200 is formed by its elongated housing 201, which in the illustrated embodiment, has an elongated linear rod-like shape. The elongated housing 201 extends from a proximal end 202 to a distal end 203 along a longitudinal axis A-A (FIG. 4). The elongated housing 201 is a tubular structure that is specifically sized and shaped for insertion into the human vagina so that pH and/or temperature measurements can be taken either in the vaginal tract or at the cervix. Of course, other elongated shapes can be utilized, including curved rods.

The elongated housing 201 has a substantially circular transverse cross-sectional profile. Of course, the elongated tubular housing 201 can have a transverse cross-sectional profile of various shapes and sizes. The exact size and shape of the elongated housing 201 will be dictated by the end use to which the vaginal health apparatus 100 is to be put, and is not to be considered limiting of the present invention unless specifically recited in the claims.

Conceptually, the elongated housing 201 comprises a proximal portion 210, a middle portion 220 and a distal portion 230. A fluid sample well 240 is formed in the distal portion 230 of the probe 200. The well 240 acts as a reservoir for holding biological fluids, such as urine, saliva, blood, cervical fluids, vaginal fluids and/or other bodily fluids. A pH sensor 250, a temperature sensor 260 and a diaphragm 270 are located within the well 240.

Turning to the handle, the general structure and shape of the handle 300 is formed by its box-like housing 301, which in the illustrated embodiment, comprises a tapered portion 310 and a generally rectangular box portion 320. The handle housing 301 provides a means by which the user can manipulate the movement of the probe 200 within the desired body lumen (when assembled as discussed below). The handle housing 301 comprises a top surface 302, a bottom surface 303, and a plurality of lateral surfaces 304 that bound the top and bottom surfaces 302, 303, thereby forming a substantially closed and hollow structure. The handle 300 generally comprises a display device 330, user controls 340-342, a first data port 314 and a second data port 315 (these elements will be discussed in greater detail below).

When the vaginal health apparatus 100 is assembled (as shown in FIG. 9), the probe 200 is removably (i.e., non-fixedly) secured to the handle 300. In other words, the probe 200 and the handle 300 are connected in a manner that allows the probe 200 and the handle 300 to be repetitively connected and disconnected without compromising the structural or functional integrity of either the probe 200 or the handle 300. In the illustrated embodiment, the probe 200 is removably secured to the handle 300 by slidably inserting the proximal portion 210 of the elongate housing 201 into a socket 519 (visible in FIG. 11) formed into the tapered portion 310 of the handle housing 301. The socket 519 of the handle housing 301 and the proximal portion 210 of the elongated housing 201 are correspondingly sized and shaped (relative to one another) so that a tight fit exists between the proximal portion 210 of the elongate housing 201 and the walls of the socket 519 of the handle housing 301 when the proximal portion 210 is fully inserted within the socket 519. This tight fit assembly provides adequate structural connectivity between the handle 300 and the probe 200 so that the probe 200 does not separate (or otherwise become dislodged) from the handle 300 during use. The proximal portion 210 of the elongated housing 201 has a tapered transverse cross-sectional area that helps facilitate slidable insertion into the socket 519 of the handle housing 301 and increases frictional engagement with the walls 521 (FIG. 11) of the socket 519.

While the non-fixed connection between the probe 200 and the handle 300 is exemplified as a tight-fit assembly, other mechanisms and structural arrangements can be implemented to effectuate the desired connection, either in addition to or in replace of the tight-fit technique. For example, one or more depressions could be provided in either the proximal portion 210 of elongated housing 201 or the walls 521 of the socket 519 of the handle housing 301 that snap-fit (or otherwise mate) with tangs (or some other protuberance) provided on the other one of the proximal portion 210 of elongated housing 201 or the walls 521 of the socket 519 of the handle housing 301. Alternatively, the outer surface of the proximal portion 210 of the elongate housing 201 and the walls 521 of the socket 519 of the handle housing 301 can be provided with corresponding threads for threaded engagement. In other embodiments, a bayonet lock, magnets, cotter pins, or combinations of the aforementioned techniques could be implemented.

A slot 211 is formed into the proximal portion 210 of the elongate housing 210 of the probe 200. The slot 211 is a linear slot that extends from the proximal end 202 toward the distal end 203 of the elongated housing 201 along a top edge of the elongated housing 201. The slot 211 is provided on the elongated housing 201 to ensure proper rotational orientation of the elongated housing 201 when the probe 200 is connected to the handle 300. A key or other protuberance 522 (FIG. 11) is provided on the wall 521 of the socket 519 of the handle housing 301. When the probe 200 is in the proper rotational orientation during assembly, the key 522 mates with the slot 211, allowing the proximal portion 210 to enter the socket. However, if the probe 200 is in an improper rotational orientation during assembly, the key 522 prohibits the proximal portion 210 from entering the socket. An indicia marker 311 on the top surface 302 of the handle housing 301 indicates the circumferential position of the key 522 (or protuberance) within the socket 519. The key/slot assembly also prevents undesired rotation of the probe 200 with respect to the handle 300 once assembly of the vaginal health apparatus 100 is achieved. As will be discussed below, proper rotational orientation of the probe 200 with respect to the handle 300 during and after assembly is important to ensure proper and stable electrical connection between the separate circuit boards of the probe 200 and the handle 300.

The probe 200 can be removed for the handle 300 for easy cleaning with warm water or mild soapy water and then rinsed with warm water. In a clinical environment, the probe 200 would need to be sterilized with something similar to CIDEX OPA solution (Johnson and Johnson). Alternately, the probe 200 could be designed with material such as PEEK and be subjected to autoclaving temperatures of about 130° C. For the illustrated embodiment, the use of non-autoclaving process is suggested. The probe 200 in this embodiment is approximately 0.40 inches in diameter and 7 inches long. Changes in dimensions can be accommodated in order to support pH measurement in other female mammals.

As will be discussed immediately below, the circuitry to be positioned within the probe 200 and the circuitry to be positioned within the handle 300 is strategically selected so that: (1) the probe 200 is as inexpensive as possible so that it can be discarded and replaced as necessary; (2) the handle 300 can be used in conjunction with different probes 200 and still prove accurate and reliable measurements; (3) all data relating to the measurements taken over periods of time is stored within the handle 300 for either internal or external processing; and/or (4) the need for calibration is minimized. As a result of this strategic separation and placement of circuitry, the handle 300 becomes the logic controller assembly of the vaginal health apparatus 100.

Figure 2:
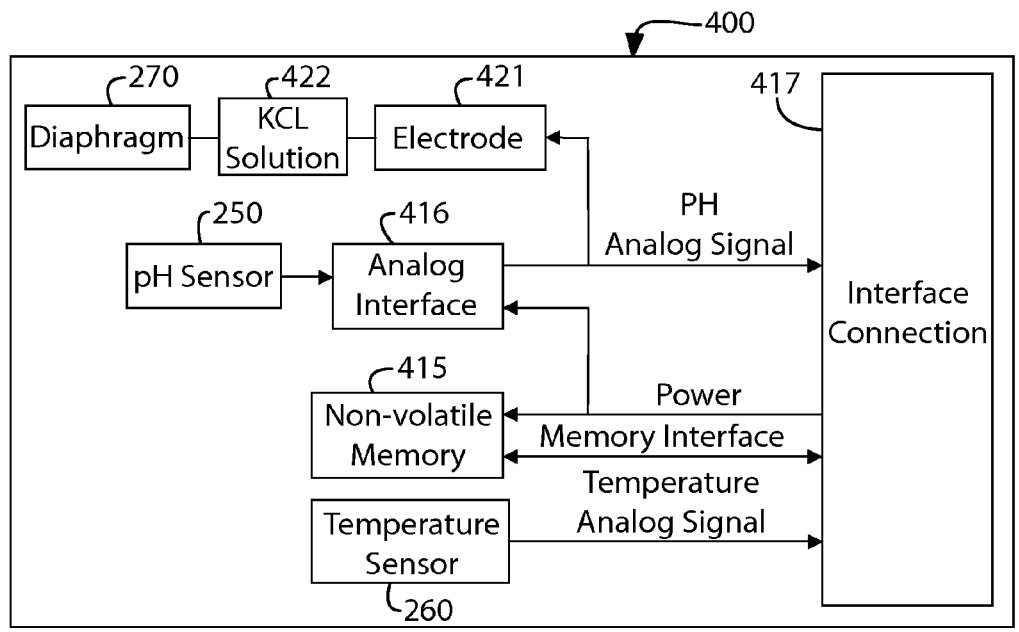
FIG. 2 is a high level electrical schematic for the probe of the vaginal health apparatus of FIG. 1.
Figure 3:
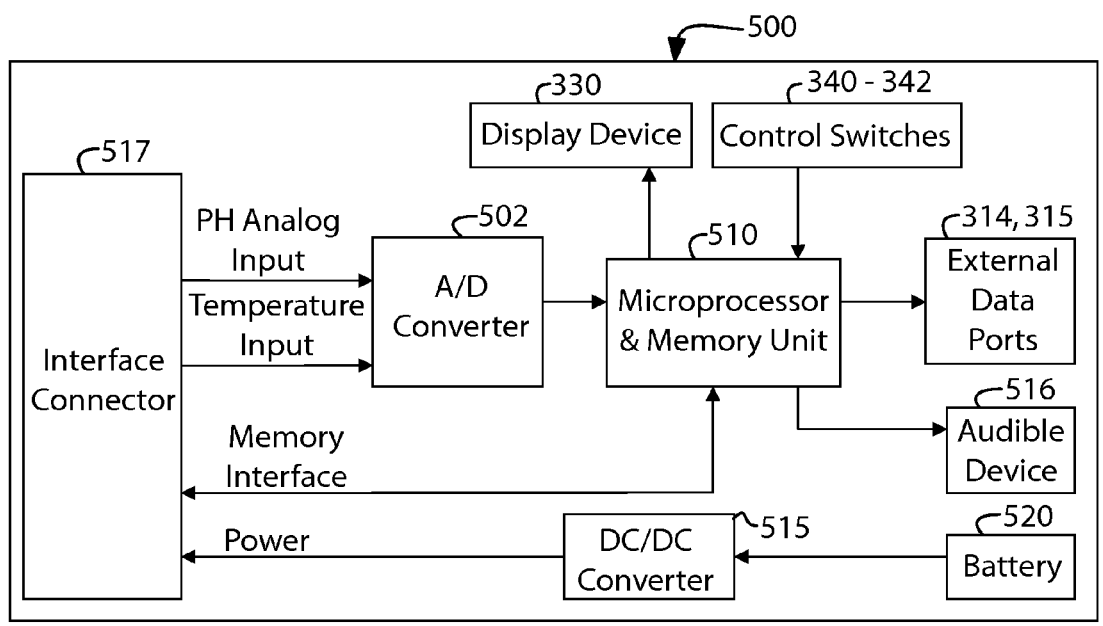
FIG. 3 is high level electrical schematic for the handle of the vaginal health apparatus of FIG. 1.

Referring to FIGS. 2-3 concurrently, the strategic separation and selection of the circuitry necessary to run the vaginal health apparatus 100 is shown according to one embodiment of the present invention. FIG. 2 is a high level electrical schematic of the circuit 400 which is located within the elongated housing 201 of the probe 200. FIG. 3 is a high level electrical schematic of the circuit 500 which is located within the housing 301 of the handle 300.

With reference to FIG. 2, the primary components of the circuit located within the probe 200 are the pH sensor 250, an analog interface circuit 416, a reference electrode 421, the temperature sensor 260, the diaphragm 270, KCL solution 422, a non-volatile memory 415 and an interface connector 417. All of these components are operably coupled via a circuit board, which is located within the elongated housing 201, as is well known in the art.

The pH sensor 250 is preferably an ISFET, which is a semiconductor device which has the metal gate replaced with a hydrogen-ion sensitive layer. The ISFET 250 is the primary element in measuring the hydrogen ion concentration (i.e., the pH) of the biological fluid to be measured with the vaginal health apparatus 100. When the hydrogen ions contact the gate sensitive layer of the ISFET 250, the voltage between the gate and source of the ISFET is influenced. The reference electrode 421 is required to close the electrical circuit loop. The analog circuitry 416 drives the electrode 421 in order to maintain a constant current through the drain and source of the ISFET 250. It is this drive voltage change that is used as the pH output signal and used by the A/D converter 502 (which located on the circuit 500 within the handle 300) to measure pH of the biological fluid under examination. The reference electrode 421 is preferably a typical Ag/AgCL coated wire and is placed in the KCL solution 422. The diaphragm 270 is the conduit between the KCL solution 422 and the biological fluid being measured. While the pH sensor is preferably an ISFET, in some embodiments of the invention the pH sensor can be a combination of ISFET and REFET (Reference FET) with a Pseudo Reference Electrode. As technology improves for the creation of the REFET, it would be easy to replace the combination of the ISFET and standard Reference Electrode comprised of the reference electrode 421 and KCL solution 422. For example the ISFET and REFET could be produced on the same substrate with a platinum electrode which may consist simple of an evaporated layer of Pt deposited on the ISFET/REFET substrate. It is also possible for a totally solid-state sensing probe to be incorporated into the invention.

The temperature sensor is preferably a thermistor, and more preferably a typical NTC (negative temperature coefficient) device. While the temperature sensor is preferably a thermistor, in some embodiments of the invention the temperature sensor can be a thermocouple or infrared detector.

The non-volatile memory 415 is preferably a simple 2 wire serial memory that can be read by and written to by the microprocessor 510 (which is located on the circuit 500 of the handle 200). The interface connector 417 is preferably one or more PCB pads. The invention, however, it so limited and any suitable mechanism, technique or device that can be used to repetitively engage and disengage with a corresponding interface connector to operably and electrically couple circuits together can be used. For example, the interface connector 417 could be multi-pin connector, a USB connector, a firewire connector, or other jack or pin and socket combination.

Referring now to FIG. 3, the primary components of the circuit 500 located within the handle 300 are the microprocessor 510, A/D converter 502, the display device 330, control switches 340-342, the first and second data ports 314, 315, an interface connector 517, a DC/DC converter 515, an audible device 516, and a battery 520. All of these components are operably coupled via a circuit board, which is located within the handle housing 301, as is well known in the art.

The control switches 340-342 are used to select various functions of the vaginal health apparatus 100, such as power on/off, calibration, start/stop measurements, etc. These functions can be displayed via menu screens on the display device 330. The display device 330 is preferably an LCD display panel, such as a full graphic display or a simple segmented and icon based display. However, the display device 330 can be any type of device used to visibly display information or status, such as one or more LEDs, OLED display, or other types of screens, such as plasma or LED.

The first and second data ports 314, 315 can be any type of wired or wireless port that can facilitate data transfer and communication between the vaginal health apparatus 100 and an external electronic device, such as a computer, cell phone, handheld data assistant, or the like. Examples of data ports include without limitation firewire ports. USB ports, min-iUSB ports, IRDA ports, serial ports (such as RS232), multi-pin ports, RF transceivers, etc.

The interface connector 517 is preferably one or more compression connectors for operably and electrically coupling with the interface connector 417 of the circuit 400 of the probe 200. As discussed above, the interface connector 517 is selected to mate with the type of interface connector 416 chosen for the probe 200. Any of the types of connectors mentioned above for the interface connector 417 can be used for the interface connector 517 of the circuit 500 of the handle 300.

The interface connectors 417, 517 are selected and positioned within the probe 200 and handle 300 respectively so that when the probe 200 is assembled/connected to the handle 300 (as described above), the interface connectors 417, 517 come into and stay in operable connection with one another so that data signals and power can be transmitted between the two circuits 400, 500. When the interface connectors 417, 517 are in operable connection, the power source 520, which is preferably in the form of a lithium coin cell battery, provides the necessary power for both of the circuits 400, 500. Additionally, pH and temperature signals generated by the pH and temperature sensors 250, 260 are transmitted to the microprocessor 510 (after passing through the A/D converter 502) for processing and or storage. Additionally, the microprocessor 510 can access and retrieve data (such as parametric data, such as properties and parametric data, that is inherent to the pH sensor 250), stored in the memory device 415 of the circuit 400.

Figure 5:
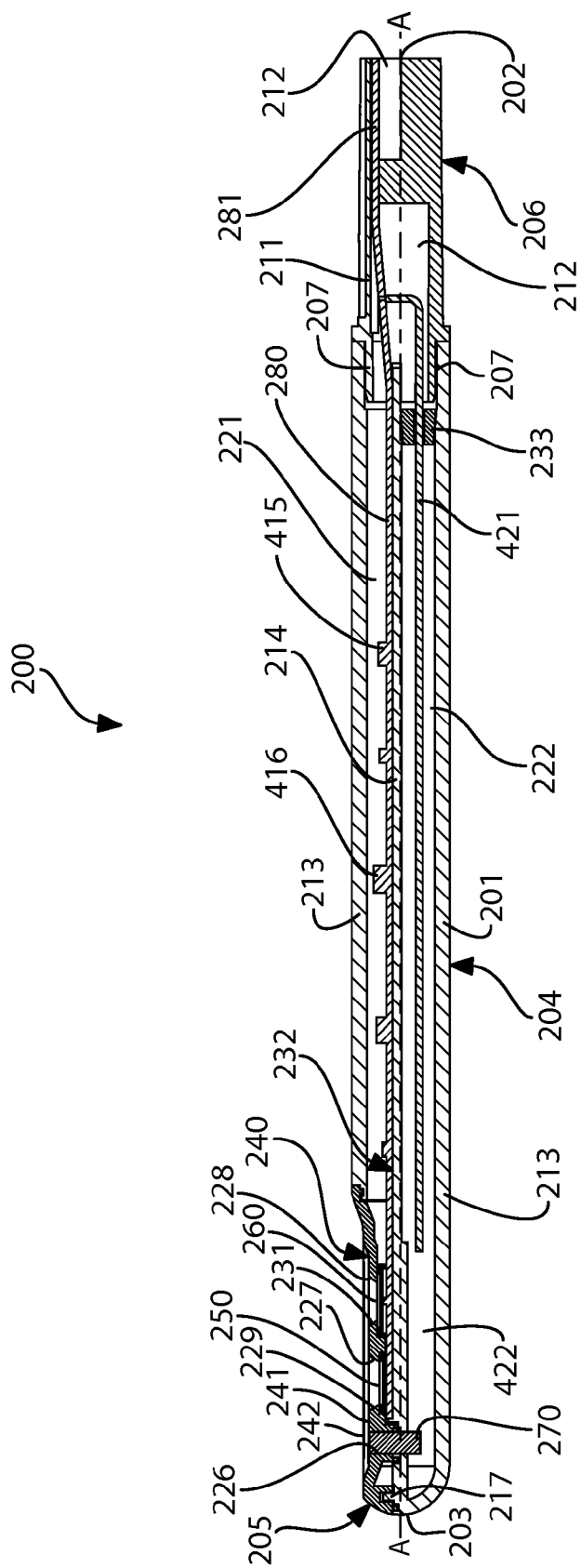
FIG. 5 is a cross-sectional view of the probe of FIG. 4 taken along view V-V.
Figure 6:
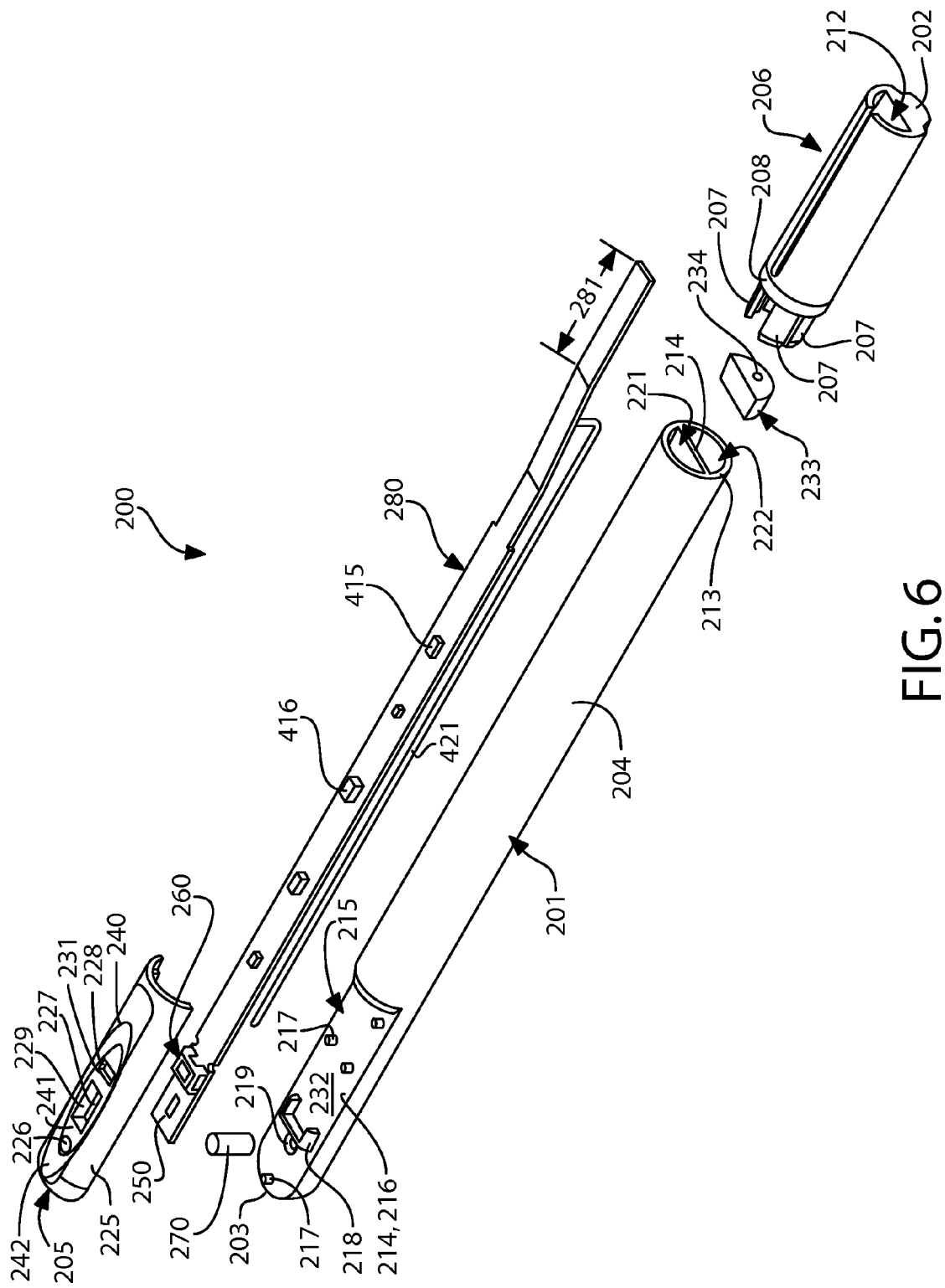
FIG. 6 is an exploded view of the probe of FIG. 4.

Referring now to FIGS. 4-6 concurrently, additional details of the probe 200 will be discussed. As discussed above, the probe 200 comprises an elongated housing 201 which extends from a proximal end 202 to a distal end 203 along the longitudinal axis A-A. The elongated housing 201 comprises a main housing portion 204, a cover 205 and a coupling 206. Preferably, the elongated housing 201 is constructed of a plastic, such as a medical grade ABS material, or other biocompatible material.

The coupling 206 forms the proximal portion 210 of the elongated housing 201 while the cap 205 extends along the distal portion 230 of the elongated housing 201. The coupling 206 comprises four spaced apart flexible tabs 207 extending from its distal edge for insertion into the internal chamber(s) 221, 222 of the main housing portion 204. When the probe 200 is assembled, the flexible tabs 207 of the coupling 206 are slid into the internal chamber(s) 221, 222 of the main housing portion 204 until a collar 208 of the coupling 206 contacts the proximal edge of the main housing portion 204. Frictional contact between the tabs 207 and the inner surface of the main body portion 204 secure the coupling 206 to the main body portion 204. The connection between the coupling 206 and the main body portion 204 can be further enhanced by using an adhesive, sonic weld, thermal weld, or any other connection techniques that are now known or later developed in the art. Preferably, the interface between the coupling 206 and the main housing portion 204 is hermetic so that fluids can not enter the elongate housing 201 at this location.

The lower longitudinal section 209 of the coupling 206 is solid while the upper longitudinal section comprises a cavity 212 that extends the entire length of the coupling 206, thereby forming a longitudinal passageway through the coupling 206. The cavity 212 is in spatial communication with the slot 211 (which was discussed above in detail). When the coupling 206 is secured to the main body portion 204 when the probe 200 is assembled, the cavity 212 of the coupling is in spatial communication with the top chamber 221 of the main body portion 204. As explained in greater detail below, this allows the circuit board 280 (the majority of which is housed in the upper chamber 221 of the main housing portion 204) to extend into the cavity 212 of the coupling 206.

As discussed above, the transverse cross-sectional profile of the coupling 206 is tapered along its longitudinal length, with the smallest area being at the proximal end 202. This allows the coupling 206 to be inserted into the socket 519 of the handle housing 300.

The main housing portion 204 comprises an outer tubular wall 213 that forms an elongated internal cavity. A transverse wall 214 that extends along the longitudinal axis A-A is provided within (and integrally formed with) the outer tubular wall 213, thereby separating the elongated internal cavity into a first longitudinal chamber 221 and a second longitudinal chamber 222. The first and second longitudinal chambers 221, 222 extend in an axial adjacent manner and are hermetically isolated from one another. The transverse wall 214 is preferably centrally arranged within the outer tubular wall 213 but can be offset from the longitudinal axis if desired. The transverse wall 214 is preferably a flat wall having planar upper and lower surfaces. The invention, however, is not so limited and the transverse wall can take on other shapes and contours if desired.

A par-cylindrical cutout 215 is provided at the distal portion 230 of the main housing portion 204, thereby exposing a portion 216 of the transverse wall 214 and creating an open end for the upper chamber 221. While the "missing portion" of the main housing portion 204 is described as a "cutout," it is not necessary for the opening to be the result of some type of cutting, punching or breaking process. It is intended that the term "cutout" merely mean an opening, which, for example, may result from the main housing portion 204 being formed in the illustrated shape during an injection molding process. Additionally, the exact shape and location of the cutout 215 can vary as desired.

A plurality of protuberances 217 (in the form of pins) project upward from the upper surface 232 of the exposed portion 216 of the transverse wall 214. The protuberances 217 are provided to mate with corresponding bores in the cap 205 to ensure proper alignment between the cap 205 and the main housing portion 204 during assembly of the probe 200. A retaining structure 218, in the form of an upstanding U-shaped wall, also projects upward from the upper surface 232 of the exposed portion 216 of the transverse wall 214. The retaining structure 218 and some of the protuberances 217 retain and align the circuit board 280 in its proper position within the upper chamber 221 when the probe 200 is assembled.

A hole/opening 219 is provided on the exposed portion 216 of the transverse wall 214 that forms a passageway through the transverse wall into the lower chamber 222 of the elongated housing 201. The holes is 219 is sized and shaped to accommodate the diaphragm 270 so that a first portion of the diaphragm 270 is exposed to the biological fluid being tested while a second portion of the diaphragm 270 protrudes into the lower chamber 222 and is in contact with the KCL solution 422.

The cover 205 is a par-cylindrical structure that is sized and shaped to correspond to the cutout 215 so that the cover 205 can enclose the cutout 215 when the probe 200 is assembled. The connection of the cover 205 to the main housing portion 204 will be described below in greater detail with reference to FIGS. 7-8. The cover 205 generally comprises an outer surface 225. The well 240 is formed into the outer surface 225 of the cover 205.

The cover 205 comprises three holes/openings 226-228 (which are located on a floor 241 of the well 240) that provide passageways through the cover 205. The opening 226 is sized and shaped to accommodate the diaphragm 270 so that it is exposed to biological fluids during use via the opening 226. The opening 227 is sized and shaped to accommodate the pH sensor/ISFET 250 so that it is exposed to biological fluids during use via the opening 227. The opening 228 is sized and shaped to accommodate the temperature sensor 260 so that it is exposed to biological fluids during use via the opening 228.

The walls 229 of the opening 227 are tapered to help funnel and direct the biological fluids into contact with the ISFET 250. The walls 231 of the opening 228 are also tapered to help funnel and direct the biological fluids into contact with the temperature sensor 260.

The ISFET 250, the temperature sensor 260, the non-volatile memory chip 415, the reference electrode 421 and the interface connector 416 are all mounted on the small printed circuit board 280. The ISFET 250 is typically mounted to the printed circuit board 280 via epoxy and wire bonds although other mounting techniques, such as compression connections, are possible. As will be discussed in greater detail below, only a portion of the ISFET 250 contains the hydrogen ion sensing portion which makes contact with the test liquid or material via the opening 227.

The non-volatile memory chip 415, which is also located on the printed circuit board 280, is utilized to store various data. Generally, the data stored in this memory 415 is referred to herein as Vital Product Data (VPD). The VPD information contains information such as probe serial number, probe manufacturer, calibration information, parametric data unique to the ISFET and temperature sensor being used, and time since last calibration. The VPD information is intended to be used by the microprocessing unit 510 in the handle housing 300. The processing unit 510 will always read the contents of the memory device 415 to identify the VPD information in order to determine what if any actions might be required by the user before measurement.

For example, in one embodiment of the invention, the VPD information stored in the memory device 415 of the probe 200 includes:

1) Serial # information (fields 00-09). This contains important information regarding build date and location.
2) Vendor Name (fields 10-24)
3) Assembly # (fields 25-2E)
4) 3 point calibration information at ambient (room temperature) (fields 30-37 in VPD_details)
5) 3 point calibration information at body temperature (98.6 F or 37 C). (fields 38-3F in VPD_details)
6) Date Last Calibrated (fields 60-65 in VPD_details)
7) Number of Measurements Since Last Calibration (fields 66-67 in VPD_details)
8) Number of pH measurements Taken (fields 68-6A in VPD_details)
9) ISFET Leakage (fields 46-47)
10) ISFET Lot # (fields 48-4F)

Storing the "Date Last Calibrated" in the memory device 415 allows the microprocessor 510 to force the user to follow proper operating procedures in order to maximize accurate measurements. For example if it is determined that the vaginal health apparatus 100 has not been calibrated for an extended period of time, say 30 days, the firmware would not allow the user to take a vaginal measurement until pH7 buffer calibration in the sample well 240 is completed.

Storing the "Number of Measurements Since Last Calibration" in the memory device 415 ensures proper calibration in the event that, even if the vaginal health apparatus 100 was calibrated within a specific time frame, but was used say 10 times without calibration, the microprocessor 510 would then force the user to calibrate to maintain accuracy. For example in a doctor's office or other clinical environment, if they used it 10 times in one day the microprocessor 510 would force the doctor to do a calibration procedure to make sure accurate measurements are taken.

Storing the "Number of pH Measurements Taken" in the memory device 415 ensures that the useful end of life of the product can be monitored. For example if it is determined that drift occurs within the vaginal health apparatus 100 (say the KCL electrolyte solution ages or gets slightly contaminated) after 2000 measurements, the vaginal health apparatus 100 can automatically notify the user that the probe 200 needs to be replaced with a new one.

By storing calibration information at room and ambient temperature in the memory device 415, more accurate pH measurements can be attained by utilizing the unique temperature characteristics of the ISFET 250. The temperature correction factor can be obtained by calculating differences in slope or absolute values. For example if the readings at 98.6° F. vary by 0.1 pH versus the readings at ambient (say 70° F.) then the microprocessor 510 can compensate for these readings when vaginal measurements are taken. So, if a user does an occasional pH7 buffer calibration in the sample well 240, the microprocessor 510 would be able to determine the 'correction factor' for a measurement at 98.6° F. Correction for tolerances associated with the thermistor 260 and series resistor can be automatically compensated for as the absolute value at 98.6° F. is stored during the manufacturing test and calibration process.

Storing the VPD information in the memory device 415 within the probe 200 allows for "plug and play" operation by the end user, thereby simplifying operation and making this a user friendly product. The storage of the VPD information in the memory device 415 within the probe 200 is also important to minimize the number and level of calibration cycles required. Inclusion of parametric data that is unique to the specific ISFET 250 and thermistor 260 being used is an important factor in reducing and simplifying the amount of required user interaction and calibration. For example, the processing unit 510 may read the field indicating that the probe was not calibrated for an extended period of time and would automatically force the user to run a single point calibration to insure proper measurement results.

As set forth and exemplified above, the VPD information contains parametric data unique to the characteristics of the particular ISFET and thermistor housed within that probe assembly. The ability to store this unique parametric data enables the firmware within the handle housing 300 to read specific data which enables more accurate measurements and simplifies user operation. The ISFET is a semiconductor device similar to a MOSFET. As such it has characteristic curves for current and voltage. The desired mode of operation for the ISFET is in a constant drain to source voltage ($V_{ds}$) and constant drain to source current ($I_{ds}$). As the characteristics curves of the ISFET change slightly from ISFET to ISFET, the absolute voltage values will change as well when implemented in the circuit. ISFETs are built on silicon wafers and thus, the parametric properties of each ISFET will vary from lot to lot and, in some instances, even vary, from wafer to wafer or device to device (even if on the same wafer). Such differences are due to tolerances and inherent variations in the manufacturing process. These differences result in slight variables in ISFET characteristic such as ISFET leakage current, drain-source voltage/current curves, capacitance, etc. As stated earlier, the gate portion of the ISFET is replaced with an ion sensitive layer which can consist of material such as $Si_3N_4$, $Al_2O_3$ or $TA_2O_5$. Variations in the ion sensitive layer will also contribute to the characteristics of the ISFET. The combination of these ISFET characteristics along with temperature determines the slope and absolute voltage for a given pH. Thus, one ISFET placed in the circuit may exhibit a slope voltage per pH characteristic of say 55 mv/pH while another ISFET may produce a slope characteristic of 54 mv/pH. In addition, the absolute voltage value generated by the circuitry for a particular ISFET placed in a fixed buffer solution will vary among ISFETs. It is these variances and others that effect the parametrics of the ISFET/probe combination that require memorization and are stored in the VPD within the probe assembly.

All of these unique characteristics add up to make each and every ISFET 250 slightly unique, even when from the same wafer. Thus, when the ISFET 250 is put into the circuit 400 in the factory, the slope of each ISFET 250 and the absolute voltage value for a particular pH value will be different.

Also how the ISFET 250 drifts with time due to leakage current will be different since the leakage current of each device will be unique. In the case of ISFETs, variables also exist regarding the gate membrane material application which will certainly have an effect as well. Each ISFET will also have unique characteristics regarding drift with temperature. So, by storing the parametric data that is unique to the exact ISFET 250 being used in the completed probe 200, the vaginal health apparatus 100 can compensate for as many variables as possible that effect the readings. Because the probe 200 also includes other electronics, such as the op amp, the voltage reference, the Ag/AgCL electrode and electrolyte solution (which complete the ISFET circuit), the ISFET 250 is essentially profiled along with all the other components that complete the probe 200.

The following are examples of parametric data unique to the ISFET 250 (and the assembled combination of electrode 421, KCL electrolyte 422 solution and diaphragm 270) that are stored in the memory device 415:

ISFET xpH Factory Value Low Temp;
This is the value measured and programmed during final production test. These values are used to determine the ISFET slope. These values are only programmed at the factory during final testing. They will however be read by the software within the handle 300 to determine ISFET slope. The value programmed in this field should reflect the ambient temperature (25 C).

Low Temperature Value:
This is the temperature value measured during the ISFET xpH Factory Low Temperature value calibration cycle. It is written the same time as the ISFET xpH Factory Value Low Temp fields are written. This temperature should be approximately 25 C.

ISFET xpH Factory Value High Temp;
This is the value measured and programmed during final production test. These values are used to determine the ISFET slope. These values are only programmed at the factory during final testing. They will however be read by the software within the handle 300 to determine ISFET slope. The value programmed in this field should reflect the high temperature value of 39 C+/−0.1 C (98.6 F+/−0.2 F).

High Temperature Value:
This is the temperature value measured during the ISFET xpH Factory High Temperature value calibration cycle. It is written the same time as the ISFET xpH Factory Value High Temp fields are written. This temperature should be 39 C+/−0.1 C (98.6 F+/−0.2 F).

ISFET Temp Correction Value:
This is a place holder for any information that might be required for correction of pH Value with temperature. It is assumed that the ISFET xpH Factory Value will be calculated and programmed while at 25° C. The Correction Value should be for measurement at 37° C. or if correction is linear the correction required per 1° C.

ISFET Leakage Current:

This is a value in stored in uA so that it can be used to possible determine ISFET drift over time and used by software to possible compensate for this.

Referring still to FIGS. 4-6, the circuit board 280 is of an elongated shape and is positioned within the upper chamber 221. More specifically, the circuit board 280 is positioned within the upper chamber 280 and secured to the upper surface 232 of the transverse wall 214. The circuit board 280 is held in place against the transverse wall 214 via a keying system in order to make sure that the ISFET 250 and temperature sensor 260 are properly aligned with the openings 227, 228 of the cover 205 when the cover 205 is secured to the main housing portion 204 to enclose (and seal) the cutout 205.

A proximal portion 281 of the circuit board 280 extends into the cavity 212 of the coupling 206. The proximal portion 281 of the circuit board 280 comprises the interface connector 417, in the form of PCB pads, which are located on the bottom surface of the circuit board 280 for operable contact/mating with the interface connector 517 of the handle housing 300 when the vaginal health apparatus 100 is assembled.

While the circuit board 280 is located within the upper chamber 221, the reference electrode 421 extends from the circuit board 280 and into the lower chamber 222. The lower chamber 222 is filled with an electrolyte solution 422 that is buffered at a known pH, such as KCL at a pH of 7.0. The lower chamber 222 is hermetically sealed in order to prevent any leakage of the electrolyte solution 422. The sealing of the open end of the lower chamber 222 is accomplished using an electrolyte plug 233. The reference electrode 421 extends through a small hole 234 in the plug 233. The appropriate hermetic seal is then formed with an appropriate epoxy or ultrasonic or thermal welding.

Figure 7:
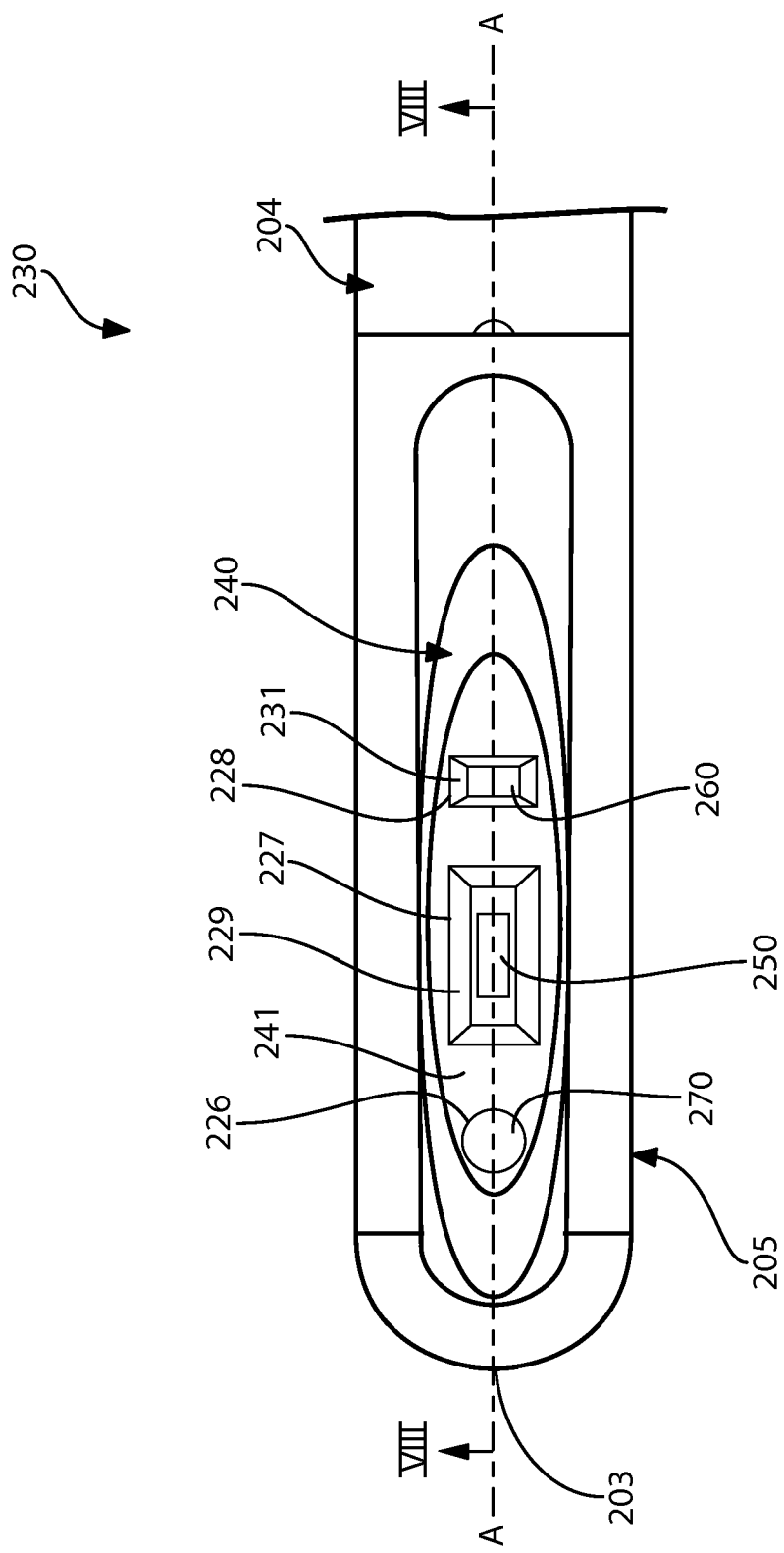
FIG. 7 is a close-up top view of the distal portion of the probe of FIG. 4.
Figure 8:
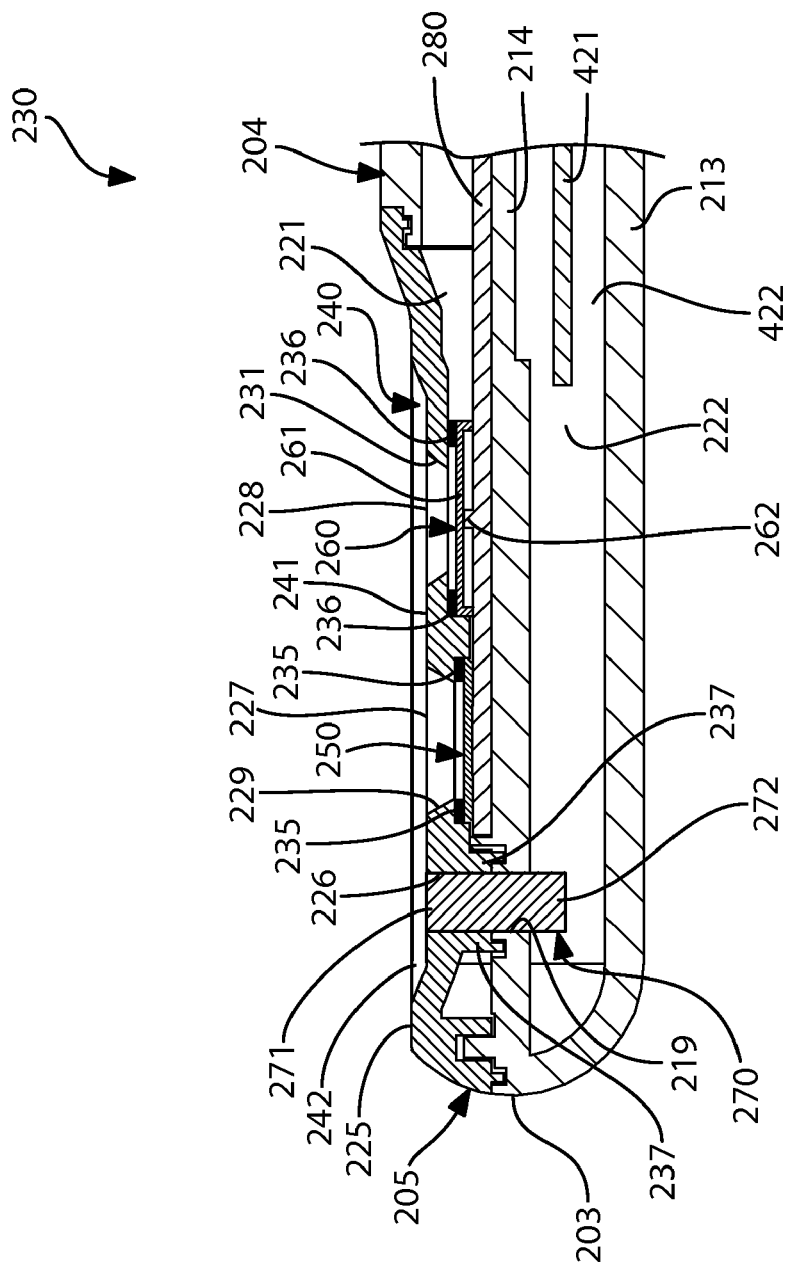
FIG. 8 is a cross-sectional view of the distal portion of the probe taken along view VIII-VIII of FIG. 7.

Referring now to FIGS. 7-8 concurrently, the construction of the distal portion 230 of the probe 200, and the relationship between its components, will be described in greater detail. As discussed above, the cover 205 of the probe 200 comprises a well 240 that acts as a reservoir for holding a biological fluid that is to be measured with the vaginal health apparatus 100. The well 240 is a depression, channel or groove formed into a top edge of the cover 205 that acts as a reservoir (or small bowl) for biological fluids. In addition, the well 240 provides a method for taking in-vitro measurements. Sample material or swabs can be taken and placed into the sample well 240 if desired.

The sample well 240 also provides a method for easy calibration and a reduction of the amount of calibration solution required. Only a small volume of buffer solution (a few drops) will be required for the calibration process. Of course, the well 240 can be modified to accommodate more or less material by easily modifying the length, width or depth of the depression.

The well 240 comprises a floor 241 and an annular rim 242 that surrounds the floor 241. The annular rim 242 provides an upstanding wall that retains the biological fluid within the well 240. The well 240 is designed into the probe 200 so that it can be easily inserted into the vagina for in-vivo measurement of the vaginal wall surface or the ectocervix. During such use, the annular rim 242 can be scraped against the vaginal wall or cervix by rotating the probe 200 so as to force fluids into the well 240.

The ISFET 250, the temperature sensor 260 and the diaphragm 270 are embedded within the floor 241 of the well 240 in order to provide an accurate pH measurement. The ISFET 250, the temperature sensor 260 and the diaphragm 270 are exposed to the exterior of the apparatus 100 via the openings 226-228, which are aligned along an axis that is spaced from and substantially parallel to the longitudinal axis A-A. Aligning the openings 226-228 on such an axis ensures that the diaphragm 270, ISFET 250 and temperature sensor 260 all make contact with the sample material, allowing for an accurate pH measurement and/or temperature measurement.

The wall 229 of the opening 227 that surrounds the ISFET 250 is tapered/sloped to assist in capturing and directing the fluids and/or tissue in contact with the ISFET 250. Similarly, the wall 231 of the opening 228 that surrounds the temperature sensor 260 is also tapered/sloped to assist in capturing and directing the fluids and/or tissue in contact with the temperature sensor 260.

A fluid tight seal is required around the ISFET 250 and the temperature sensor 260 in order to prevent contamination or leakage of fluids into the electronics of the probe 200. However, both the ISFET 250 and the temperature sensor 260 need to remain exposed via the openings 227, 228 in order to take accurate pH and temperature measurements.

The hermetic seal of the opening 27 about the ISFET 250 can be accomplished by various means, such as an epoxy, O-ring or gasket seal. In the illustrated embodiment, a gasket 235 is compressed between the bottom surface of the cover 205 and the perimeter portion of the ISFET 250. The gasket 235 can be held in place by the plastic cover 205 or could be over molded onto the bottom surface of the cover 205.

The temperature sensor 260 preferably comprises a metal cap 261 that is placed over and covers a thermistor 262. The metal cap 261 can be constructed of a medical grade stainless steel or other metal which is a good thermal conductor. A small space/gap exists between the metal cap 261 and the thermistor 262. The space/gap, in one embodiment, is approximately 0.005 inches. This space/gap is filled with a material, such as an epoxy, having high thermal conductivity but that is electrically non-conductive. Filling this gap/space with such a material reduces the thermal time constant of taking a temperature measurement. In the illustrated embodiment, a surface mount thermistor is used. However, a typical bead thermistor can also be utilized and adhered to the stainless steel cap 262.

The metal cap 261 keeps the thermal time constant as low as possible and should have as small an area as practical with a thickness kept as thin as practical (0.10" in this embodiment). The temperature sensor 260 is used for measuring the temperature of the vagina or cervix during the measurement. Although an exemplary application of the temperature sensor 260 is detailed, those skilled in the art will appreciate that an alternate, temperature sensing device can be used, such as a thermocouple or infrared detection. The temperature sensor 260 also provides temperature information used during the manufacturing process and calibration in order to allow for proper thermal compensation of the pH reading.

As with the ISFET 250, it is necessary to create a fluid tight seal about the opening 228 while leaving the metal cap 261 exposed to the biological fluid/tissue to be tested via the opening 228. The hermetic seal of the opening 228 about the metal cap 261 can be accomplished by various means, such as an epoxy, O-ring or gasket seal. In the illustrated embodiment, a gasket 236 is compressed between the bottom surface of the cover 205 and the top surface of the metal cap 261. The gasket 236 can be held in place by the cover 205 or could be over molded onto the bottom surface of the cover 205. The gasket 236 is compressed the proper amount when the plastic cover 205 is secured to the main housing portion 204.

The gaskets 235, 236 are sufficiently compressed when the plastic cover 205 is secured to the main housing portion 204. The cover 205 is permanently secured to the main housing portion 204 so that the cutout 215 is hermetically sealed, thereby sealing the distal portion of the upper chamber 221.

The interface between the cover 205 and the main housing portion 204 can be sealed by epoxy, a sonic weld, a thermal weld or another compressed gasket.

The diaphragm 270 is positioned within and extends through the opening 226 of the cover 205 and the opening/hole 219 in the transverse wall 214 of the elongate housing 201. A first portion 271 of the diaphragm 270 is exposed to the biological fluid being measured via the opening 226 while a second portion 272 of the diaphragm 270 extends into the lower chamber 222 via the hole 219. The second portion 272 of the diaphragm 270 is in contact with the KCL solution 422 within the lower chamber 222 of the elongate housing 201. The walls 237 of the opening 226 extend transversely (relative to the longitudinal axis) and contact the transverse wall 214 so as to form a seal at the interface between the two, thereby keeping the upper chamber 221 (and the circuit board 280) hermetically sealed from fluids and contamination.

The diaphragm 270 can be either a ceramic or PTFE material that is commonly used in pH probe assemblies. The diaphragm 270 allows the hydrogen ion flow between the reference electrode 421 and the KCL solution 422 and the measurement fluid. The diaphragm 270 provides the electrical connection between the reference electrode 421 and the biological fluid being measured.

Figure 10:
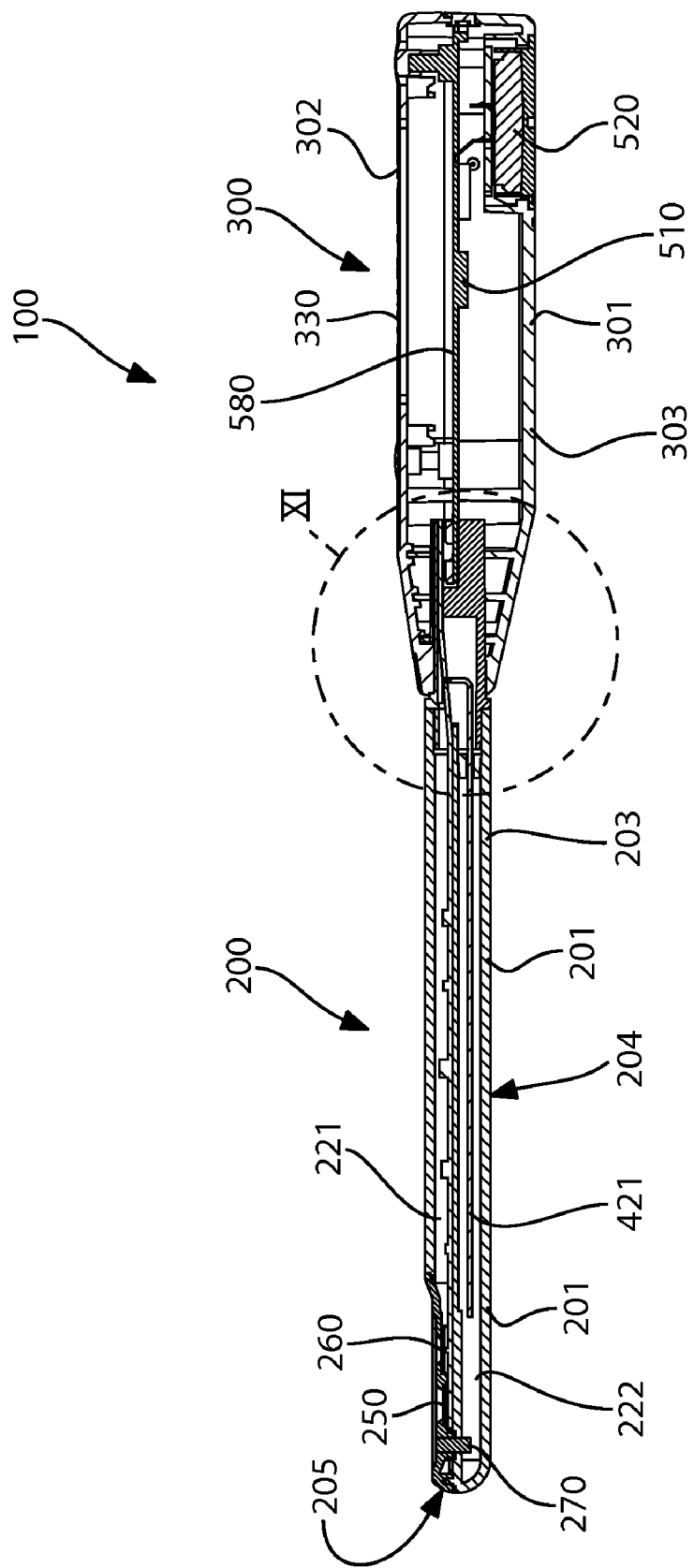
FIG. 10 is a cross-sectional view of the vaginal health apparatus along view X-X of FIG. 9.
Figure 11:
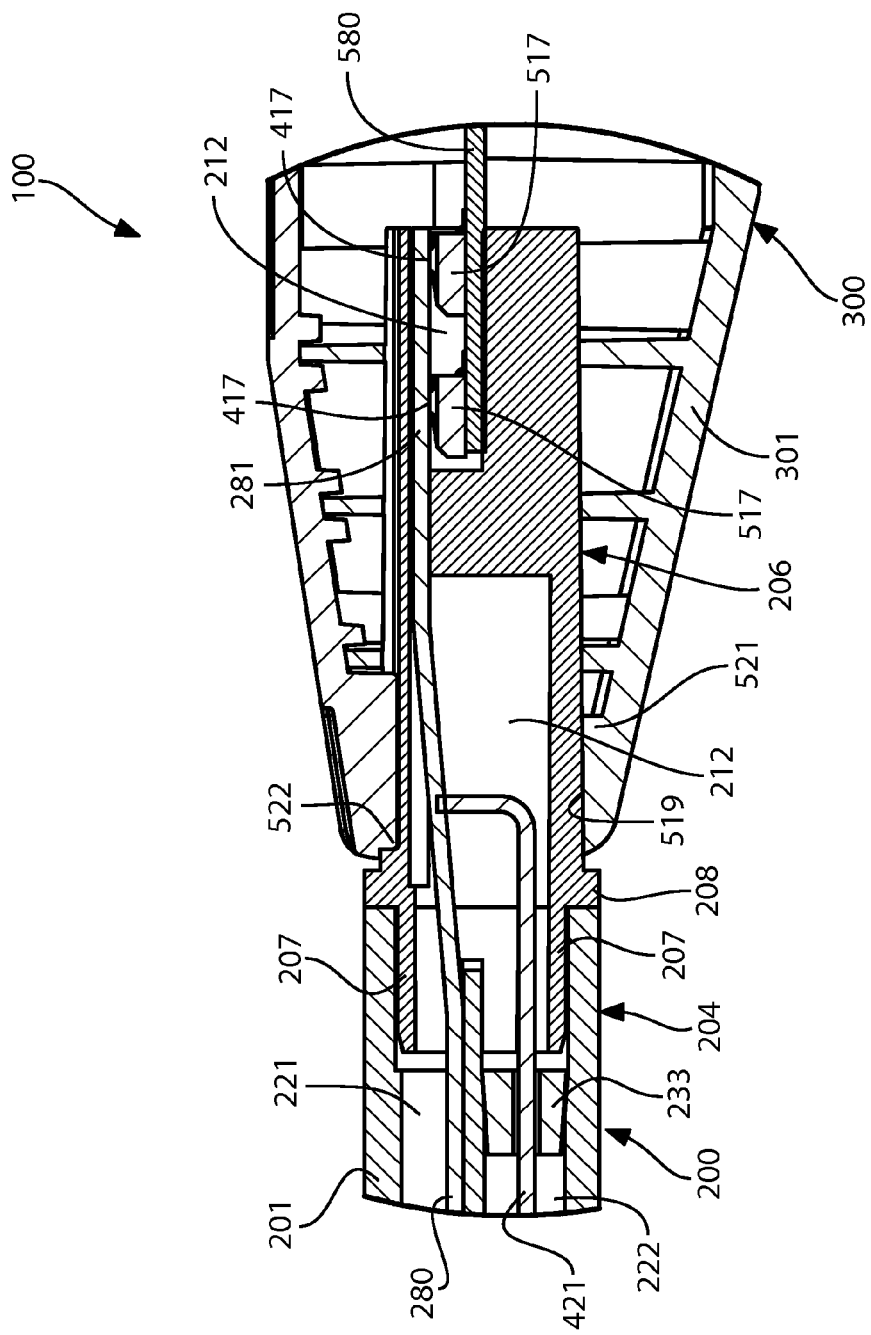
FIG. 11 is a close-up view of area XI of FIG. 10.

Referring now to FIGS. 10-11 concurrently, the assembly of the probe 200 to the handle 300, which also operably couples the measuring circuit 400 to the logic circuit 500, will be discussed in greater detail. When the probe 200 is assembled to the handle 300, the proximal portion 210 (i.e., the coupling 206) of the probe 200 is inserted into the socket 519 of the handle housing 301 as discussed above. The assembly of the probe 200 to the handle 300 results in the operable connection of the probe circuit 400 (FIG. 2) to the logic circuit 500 (FIG. 3) because the gold plated PCB pads 417 of the printed circuit board 280 of the probe 200 come into operable and electrical connection with the compression connectors 517 of the printed circuit board 580 of the handle 300. The gold plated PCB pads 417 are configured in a manner such that the Ground signal pin, which is the return path for the supply voltage provided by the housing 300, is slightly longer (about 0.020") at the proximal 210 end than the other gold plated PCB pads. The purpose of this extended pad is so the first electrical connection made when inserting the probe 200 into the housing 300 is the ground pin. This first "make" connection helps in providing a discharge path for any erroneous charges that may be residing in the probe 200 or housing 300 assemblies. The other function of this elongated pin is to provide the last connection when disengaging the probe 200 from the housing 300 thereby keeping the ground connection in place as the last signal to disengage or "break". This type of configuration is commonly referred to as 'make before break' and helps prevent damage to the electrical components within both the probe 200 and housing 300 assemblies due to electro-static discharge or capacitive discharge when engaging and disengaging these assemblies.

Referring now to FIGS. 12A and 12B, a protective cap 600 for the distal portion 230 of the probe 200 is illustrated alone and secured to the distal portion 230 of the probe 200. The cap 600 is preferably constructed of an opaque material that is pliable. As illustrated in FIG. 12A, the cap 600 is in an open position. In FIG. 12B, the cap 600 is in the closed position and secured to the probe 200 in the intended manner.

The cap 600 generally comprises a lid 610 and a base 620. The lid 610 is pivotably connected to the base 620 via hinges 601 so as to be capable of rotation about axis B-B. A latch assembly 630, 631 is provided to lock the cap 600 in a closed position.

The lid 610 comprises a bottom surface 611 and a channel 615 formed into the bottom surface 611. The channel 615 has an open end 616 and a closed end 617. A first rim 618 protrudes from the floor 619 of the channel 615 at the open end 616. A second rim 614 extends along the perimeter of the lid 610 and protrudes outward from the bottom surface 611.

Similarly, the base 620 comprises a top surface 621 and a channel 625 formed into the top surface 621. The channel 625 has an open end 626 and a closed end 627. A first rim 628 protrudes from the floor 629 of the channel 625 at the open end 626. The base 620 further comprises a plurality of legs 640 for supporting the base at a desired height.

When the lid 610 is rotated about axis B-B to the closed position, the bottom surface 611 of the lid 610 comes into contact with the top surface 621 of the base 620. As a result, the two channels 615, 625 come together to collectively form an internal cavity that is sized and shaped to accommodate the distal portion 230 of the probe 200. This internal cavity has an open end through which the remaining length of the probe 200 can protrude (as shown in FIG. 12B). The opposite end of the internal cavity is closed.

When the cap 600 is in the closed position, the rim 614 of the lid 610 becomes compressed between the lid 610 and the top surface 621 of the base 20 so as to form a gasket seal between the lid 610 and the base 620. Similarly, when the cap 600 is in the closed position and the cap is secured to the probe 200 (as shown in FIG. 12B), the rims 618, 628 come together to collectively form an annular rim that acts as a gasket seal between the outer surface of the probe 200 and the floors 619, 629 of the cap 600. The rims 614, 618, 628 are made of material that has a sufficiently low durometer value so as to create the gasket type seals. The latch assembly 630, 631 keeps these gasket seals in tact when locked. As a result, when the cap 600 is closed and secured to the probe, the distal portion 230 of the probe 200 (including the well 240) is housed in the sealed internal cavity of the cap 600. Moreover, because the cap is constructed of opaque material, this internal cavity is substantially free of visible light (i.e., it is dark).

The cap 600 serves multiple purposes in this particular aspect of the invention. The primary function of the cap 600 is to protect the ISFET 250 during storage. Scratching of the ISFET 250 can damage the ion sensitive membrane and effect operation. A secondary function of the cap 600 is to create a hermetically sealed internal storage cavity about the distal portion 230 of the probe 200 (which includes the ISFET 250, temperature sensor 260 and diaphragm 270) to keep the diaphragm 270 slightly hydrated between uses. A drop of de-mineralized or distilled water can be placed in the cap 600 once the probe 200 is laid in the channel 625 and then sealed with the latch mechanism 330, 331.

The third function of the cap 600 is to act as a support mechanism for the vaginal health apparatus 100 so that the sample well 240 of the probe 200 is held level and not susceptible to tipping during measurements. The legs 640 of the cap act as supports to raise the tip of the probe 200 so that the longitudinal axis A-A of the probe 200 is substantially horizontal when the distal portion 230 of the probe 200 is resting within the channel 625. Thought of another way, because the bottom edge of the probe 200 is non-coplanar with the bottom surface 303 of the handle 300, the probe 200 will have a tendency to tip/tilt. Thus, the height of the legs 640 is selected so that when the distal portion 230 of the probe 200 is resting within the channel 625, the bottom surfaces of the legs 640 are substantially coplanar with the bottom surface 303 of the handle 300.

A fourth function of the cap 600 is to provide a cover for the ISFET 250 during the sample well measurement and/or during calibration. The ISFET 250 is a semiconductor device, and as such, is susceptible to UV light. Various manufacturers of ISFET's have different levels of sensitivity and generally measurement isn't affected greatly unless directly exposed to sunlight or high intensity lighting. However, by placing the biological fluid to be measured in the well 240 and securing the cap 600 to the probe 200, the measurement will always be taken in a dark environment which would reduce the potential effects of UV light impacting the reading. This "dark" environment more accurately simulates the condition within the vaginal canal and cervix or of the environment of the fluid within the body.

Figure 13A:
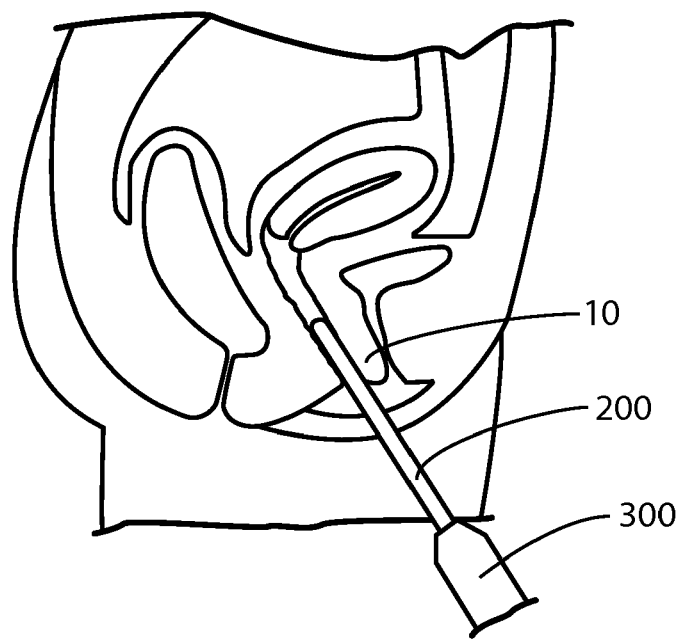
FIG. 13A is a schematic of the vaginal health apparatus of FIG. 1 inserted into the vagina of a humane female and positioned for vaginal pH and temperature measurements.

Referring now to FIG. 13A, the insertion of the probe 200 into the vaginal cavity is illustrated for measuring pH within the vagina. When inserted, the well 240 makes contact with the vaginal wall 10. The vaginal walls 10 make contact with each other and separate as the probe 200 is inserted. The vaginal wall 10 is coated with mucus membrane with a muscular tissue underneath which then forms around the probe 200 and into the well 240. The well 240 allows for the collection of the mucus fluids from the vaginal wall 10. The well 240 of the probe 200 is typically placed in the lower portion of the vaginal canal (approximately 1 to 2 inches). Upon the user selecting the measurement function via the user controls 340-342, the pH will be measured by the ISFET 250 and the user will be notified with an audio tone at completion of the measurement. The measured pH will be shown on the LCD screen 330 and saved within the memory device within the handle 300 (which is incorporated into the processor 510, but may be a separate device). This stored data is stored along with a date and time stamp so that the data can be retrieved, analyzed and compared to later measurements according to known algorithms or relationships to determine a physiological condition in a mammal, such as fertility status.

Figure 13B:
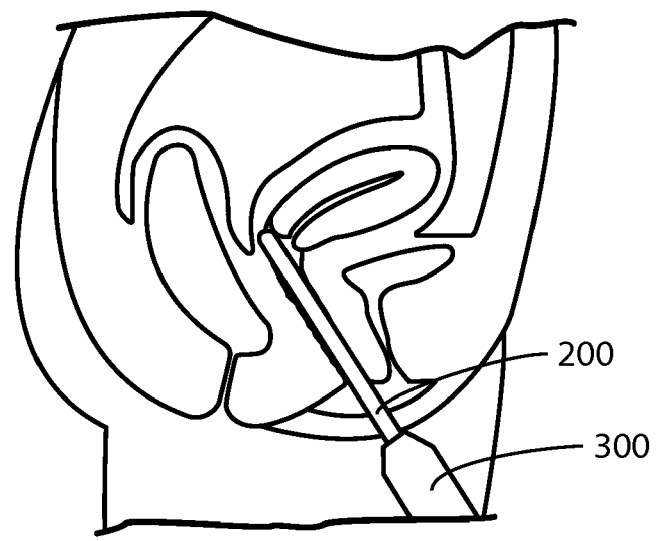
FIG. 13B is a schematic of the vaginal health apparatus of FIG. 1 inserted into the vagina of a humane female and positioned for cervical pH and temperature measurements.

FIG. 13B shows the placement of the probe 200 further up the vaginal cavity and making contact with the ectocervix area of the cervix. The well 240 makes contact with the ectocervix and collects cervical fluid for measurement. As stated earlier, the measurement of the cervical pH can be a useful aid in determining the fertility cycle of the female mammal. The probe 200 would typically be inserted about 4 to 5 inches in the vaginal canal in order to make contact with the cervix. The device as shown provides a simple and reliable method of measuring the cervical fluid to determine a condition, such as fertility status.

Figure 14:
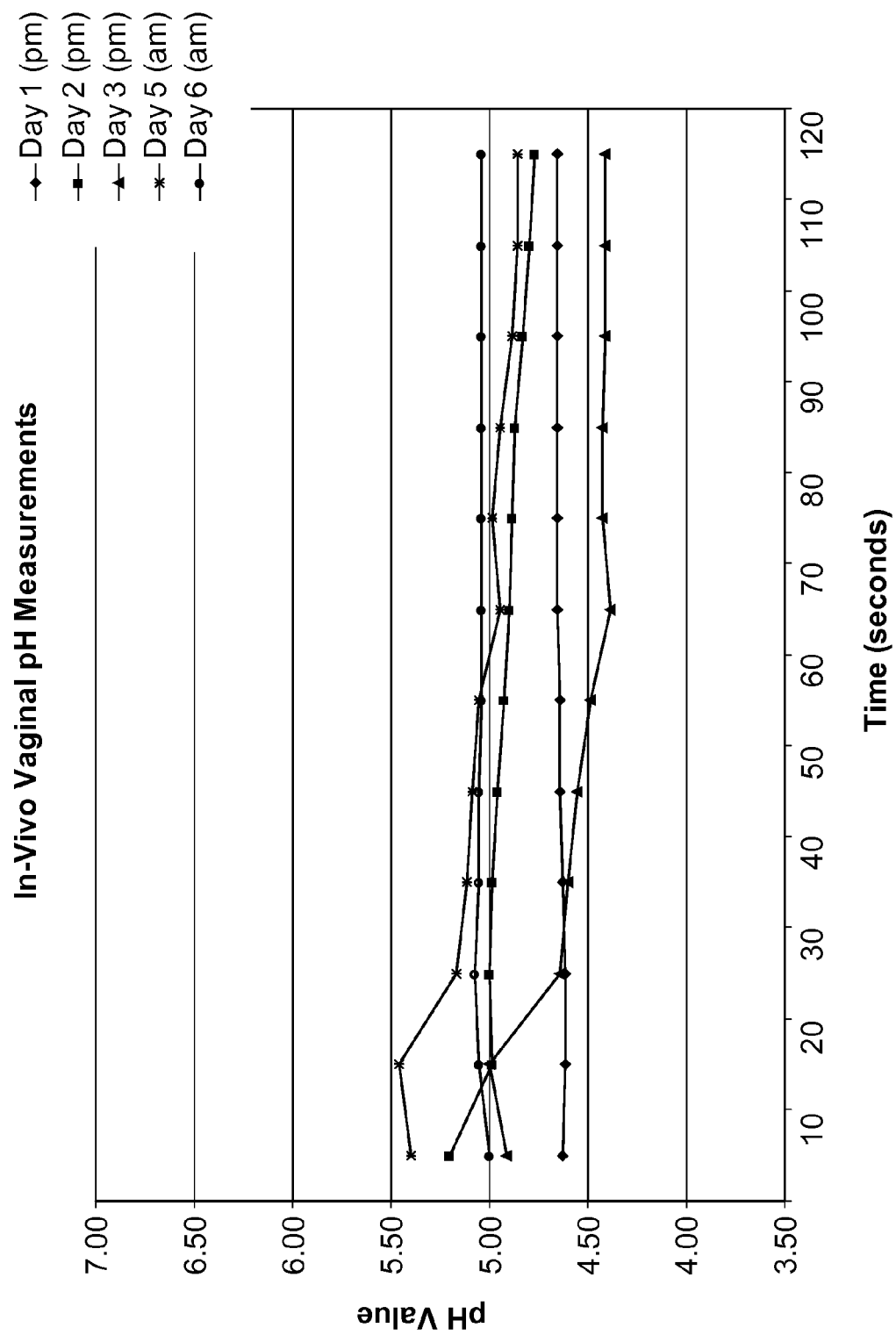
FIG. 14 is a graph of in vivo pH measurement versus time for a human female subject over a six day period wherein readings were taken every ten seconds over a two minute period.

FIG. 14 is a graph of a 6 day plot of in-vivo vaginal pH measurement using the above described invention. The data was gathered from a human female approximately age 55 and in good health. The woman was post menopausal and used the device daily for a period of 6 days. Readings were sampled every 10 seconds over a 120 second period and recorded. Data was transferred from the device 100 through the RS232 serial port 314 and ported into an Excel spreadsheet. The data displayed represents the pH recorded during the test period. It shows stable readings after a short initial settling time. The final values over the 120 second measurement period were stable and within a range of 4.41 to 5.04 over the 6 day period. No special handling or calibration was performed during the 6 day usage other than simple cleaning with warm water. Periodic calibration with pH7 buffer utilizing a few drops in the sample well after extended periods of non-use is recommended to guarantee the accuracy of measurements. If the apparatus 100 were not used for an extended period of time, the logic unit 510 would notify the user to proceed with a simple calibration procedure before taking the vaginal measurement.

Figure 15:
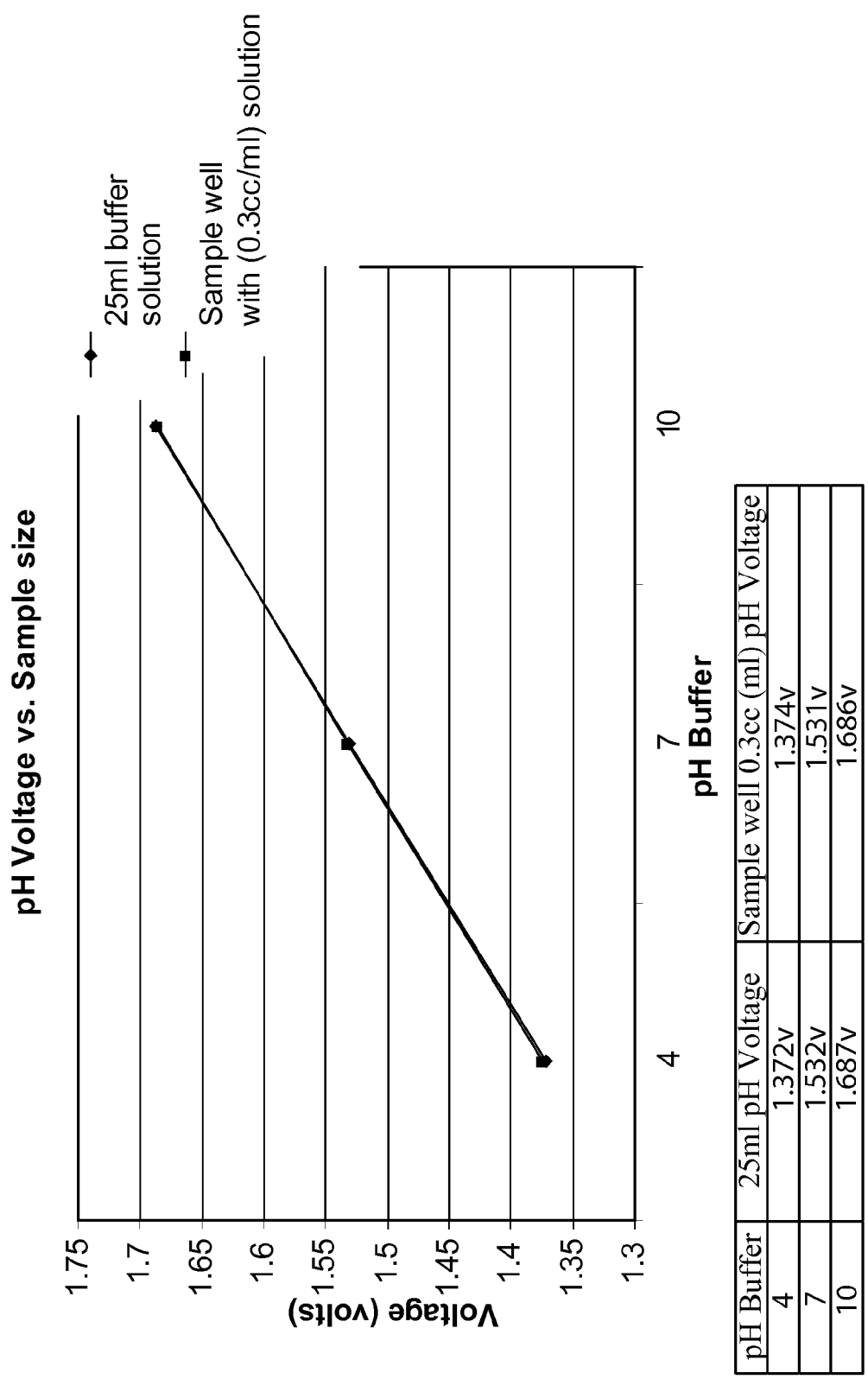
FIG. 15 is a data chart and corresponding graph of pH measurements versus voltage of three different pH buffers based on sample size so that effects of the well size on pH readings could be evaluated.

An additional test was performed to compare pH buffer measurements based on sample size. FIG. 15 is a graph of the pH voltage measured from the apparatus 100 when the probe 200 was inserted into 25 ml of buffer solution and then compared against 0.3 cc/ml of solution placed into the sample well 240. The device 100 was allowed to stabilize for 5 minutes before measurements were recorded and cleaned in water and dried between measurements. A syringe was used to insure constant amount of solution was placed into the sample well 240. As the data shows, there is no significant difference in the measurement taken in the sample well 240 vs. the 25 ml solution. The readings are typically within 1 mv which converts to a pH variance of about 0.02 pH. The data proves that the sample well 240 is of appropriate size to accurately measure small samples of solutions. It should be noted that in this implementation of the invention about 40% of the sample well area was occupied by the thermistor and therefore, it is likely that the results would be similar with <0.2 cc/ml of solution as that is all that was required to submerse the ISFET 250 and the diaphragm 270 required for the pH measurement.

Figure 16:
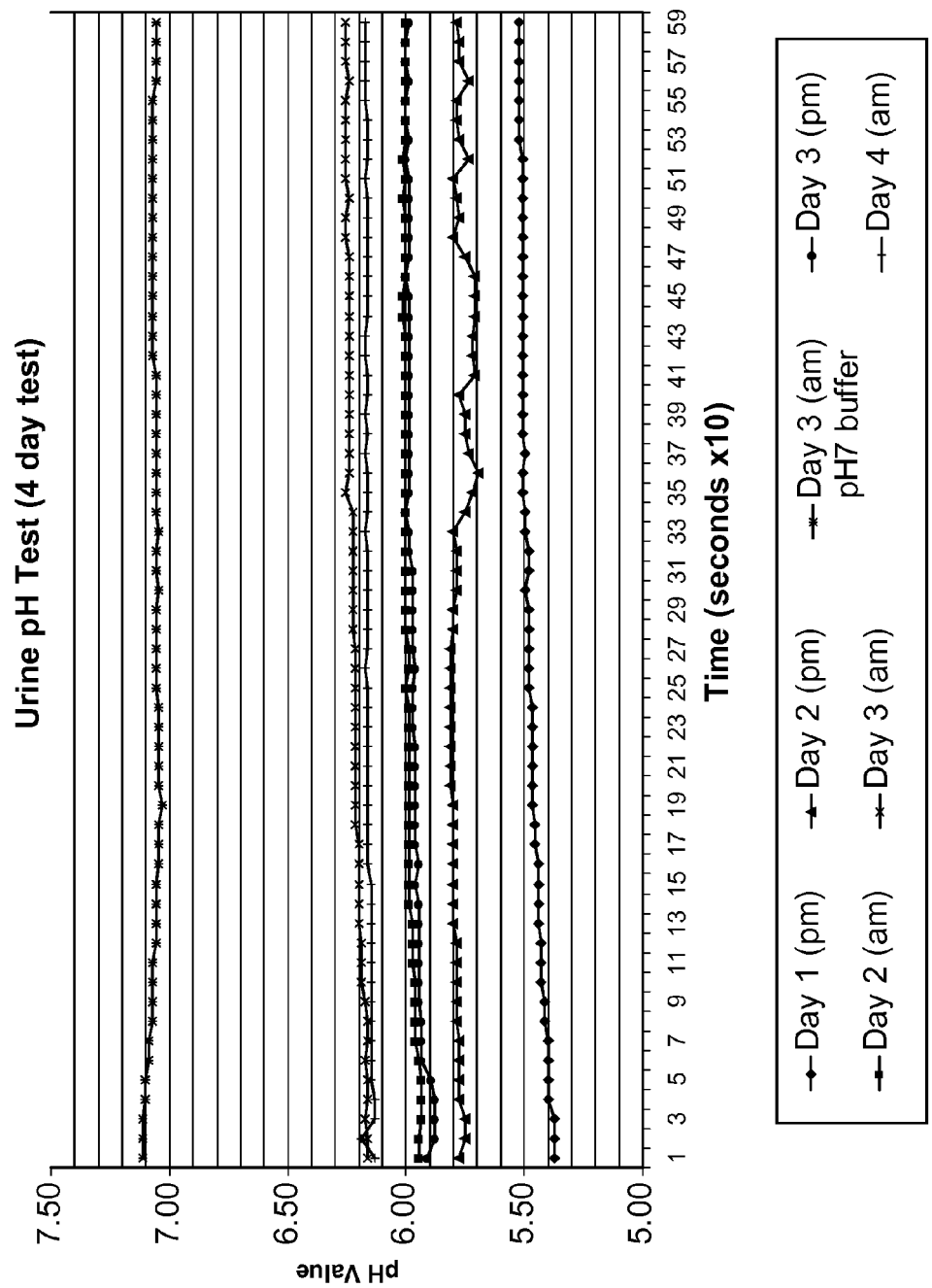
FIG. 16 is a graph of measured pH versus time for urine over a four day period wherein the urine was externally measured in the sample well.

As the results above for the sample size comparisons indicate, that there is no significant difference in the sample size test results. Therefore a test was performed to measure urine in the sample well. The device 100 was calibrated with pH7 buffer in the sample well 240 prior to the start of the test. FIG. 16 shows the results of this 4 day test. Sampling was done twice daily, once in the early morning as soon as wakening and again in later afternoon prior to a meal. No calibration was done during the period however an additional test was preformed on day 3 using pH7 buffer solution in place of urine. This test was done to verify the continued accuracy of the measurements since calibration was not preformed between urine measurements. The data shows the device 100 was still accurate within 0.05 pH after 4 days of use w/o any daily calibration required. The probe 200 was cleaned with warm water and lightly patted dry with no special storage of the probe 200 between uses. The data shown was sampled every 10 seconds over a 10 minute (600 second) period and recorded in the memory of the logic circuit 500. Data was transferred from the RS232 serial port 314 and imported into an Excel spreadsheet for plotting. The test subject was a 55 year old male in good health. Samples were taken in the morning and late afternoon in a small paper cup with 5 drops transferred into the sample well. The pm samples were taken 5 hours after a mid-day meal while the am sample were taken early in the morning before any meals and at least 10 hours after the last meal. The data shows stable readings throughout the measurement period.

Figure 17:
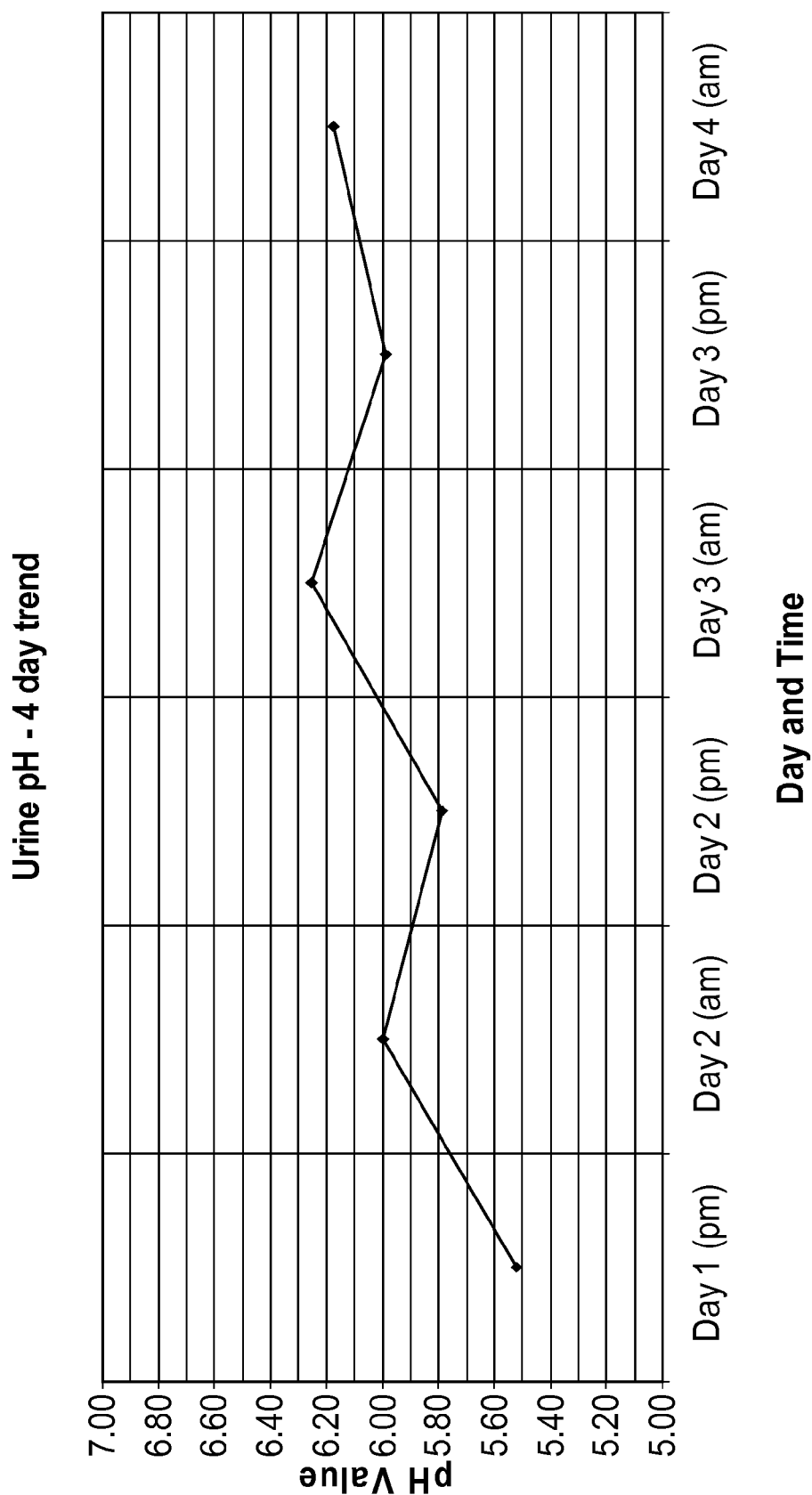
FIG. 17 is a four day trend line graph of the final urine pH measurements of FIG. 16.

FIG. 17 shows a plot of the final readings after the 10 minute period and shows the trend line after 4 days. Diet was not recorded during the test period to see if this had contributed to the positive trend line. It would be simple to duplicate this process over a larger test subject sample and monitor diet to determine the effect of diet on urine pH.

The invention accurately measures small volumes of other mammalian fluids. Besides the example of urine testing explained in the text above, examples of other fluids would be saliva or blood. By utilizing the sample well 240, the device 100 can easily be used to monitor urine pH. A small sample of about 0.3 cc (4 or 5 drops) of urine placed in the sample well will generate an accurate urine pH reading. By utilizing the automatic recording function on the device 100, these readings can be automatically stored and monitored so that the user can be notified if any significant changes have occurred over a period of time.

As mentioned above, the device 100 can be inserted further into the vagina and make contact with the ectocervix area of the cervix. Monitoring of pH of the cervix can be helpful criteria in determining the fertility cycle of the female. The design of the device is such that it also monitors vaginal or cervical temperature to monitor basil body temperature (BBT). It is a well know fact that BBT changes as much as 1° F. during the ovulation cycle and can be used as another indicator of the fertility cycle. The ability of the device 100 to store both the pH and temperature readings over an extended period of time allow the device and software to create a profile of the female mammals menstrual cycle. The ability of the device to transfer this data to a computer can be a valuable aid in analyzing and predicting the ovulation period for women with difficulty in conception.

The device 100 also monitors the vaginal pH, which can be a useful tool in the monitoring of Estrogen or Hormone Replacement Therapy (HRT). Women during or post menopause can have elevated levels of vaginal pH without having symptoms of BV. The device 100 can easily store the vaginal pH readings prior to and during the HRT in order to assist in the effectiveness and regulation of Estrogen replacement therapy.

The inventive apparatus 100 is capable of measuring pH with an accuracy of 0.1 pH or better and can record measured pH values for future reference. The device 100 has the capability of recording multiple readings of pH value, date and time of the measurement and logging of these readings so that automatic user notification can be made should an unusual change in pH value occur. The amount of readings stored is strictly dependant on the size of memory within the logic unit. It would be easy and inexpensive to store hundreds of readings so that long term monitoring is possible. This method of monitoring, recording and notification takes the guess work out of matching colors or keeping a written log of periodic readings. Reviewing this data and automatically detecting a noticeable chance can provide instant feedback to the user that further testing or diagnostic procedures may be required especially if other BV symptoms occur.

The following outlines the typical measurement process when utilizing the device 100 to measure pH and/or temperature within the vagina to determine fertility and/or vaginal health status. The user (or other personnel) will first insert the probe 200 of the device 100 into the vagina at a desired depth and alignment. If the user desires to determine fertility status by measuring cervical pH and temperature, the user will insert the probe 200 into the vagina until the distal portion 230 of the probe 200 is adjacent and in contact with the ectocervix area of the user. Preferably, the probe 200 is inserted so that the well 240 is aligned with the ectocervix tissue and the diaphragm 270, pH sensor 250 and temperature sensor 260 tire aligned with and in contact with the ectocervix tissue. If the user desires to determine vaginal health status (such as the existence of BV or any of the other condition discussed above) by measuring vaginal pH and temperature, the user will insert the probe 200 into the vagina until the distal portion 230 (including the well 240) of the probe 200 is adjacent and in contact with the vaginal wall of the user.

Once the probe 200 is in the desired position within the vagina, the user will initiate the measurement process by pressing the appropriate control button(s) 340, 341 and/or 342 on the handle 300. When the firmware within the microprocessor 510 (which is located in the logic unit . . . i.e., the handle housing 301) detects the control button depression (by receiving a measurement initiation signal) it will check to make sure that the probe 200 is electrically connected to the handle 300 through the interface connectors 417 and 517. If connected, the microprocessor 510 will then proceed to apply power from the battery 520 to the circuit 400 of the probe 200 through these interface connectors 417, 517 in order to read the contents of the VPD memory 415. The power supply from the battery 520 also enables (i.e., provides sufficient power to) the pH and temperature sensors 250, 260 and the remaining components of the circuitry 400. The processor 510 will verify that this is a proper probe assembly and that the contents of the VPD memory 415 are valid. If the firmware determines that the probe 200 has not been calibrated for an extended period of time based on the contents of the VPD memory 415 it will indicate to the user through the LCD 330 that the simple single point pH7 calibration process utilizing the sample well 240 is required. As discussed above, the calibration process is preferably performed in the removable cap 600 in a dark environment with a solution buffered at a known pH.

Once the microprocessor 510 detects that the device 100 is ready to take measurements, the user activates the user control 340-342 that sends a "take measurement signal" to the microprocessor 510. In response, microprocessor 510 initiates the pH and temperature sensors 250, 260. The pH and temperature sensors 250, 260 then generate an analog pH signal and an analog temperature signal indicative of the measured pH and temperature within the vagina or at the ectocervix. These analog pH and temperature signals from the probe 200 are then transmitted to and processed through the analog to digital (A/D) converter 502. Once the calibration or measurement cycle has started, the microprocessor firmware 510 will determine when these A/D signals are stable and then proceed to retrieve and use parametric data (including the slope data) from the VPD memory 415 to calculate the pH value. To determine the pH value, the firmware on the microprocessor 510 will read the current measured temperature and utilize the slope data for the ambient 25 C temp and the normal body 98.6 temp to determine any pH correction factor that may be required at the current temperature. Once this calculation is complete, an output signal will be generated by the microprocessor 510 that corresponds to the correct pH and temperature values. The output signal is sent to the LCD 330 for viewing. This pH and temperature information along with the date/time stamp from the real-time clock (RTC) will also be stored in the local memory located (incorporated into the microprocessor 510) within the handle 300.

The microprocessor 510 will then proceed to update the appropriate fields within the VPD memory 415 to indicate that a measurement was taken along with the date/time stamp of that measurement. This stored VPD information is then used for the next measurement cycle to determine how long since the probe 200 has been used and/or how many measurements have been taken with this particular probe.

As mentioned above, when utilizing the device to monitor vaginal health, the device 100 will be used to take pH and temperature measurements at the lower portion of the vaginal wall as indicated in FIG. 13A. A similar process of verification and measurement as outlined above will occur for the vaginal fluid captured in the sample well. These vaginal pH and temperature measurements would most likely be taken when an instance of infection like BV, Candidiasis (yeast infection) or Trichomoniasis is suspected. These pH readings are important criteria for diagnosing any of these infections. Continued measurements can be taken after any diagnosis to determine the effectiveness of an OTC or prescribed treatment. The device 100 will also save these readings which can be downloaded for analysis. Vaginal measurements need not only be taken when an instance of infection is suspected.

Normal periodic measurements can be taken and tracked by the processing unit to notify the user if any significant changes or trends have been detected over an extended period of time. This could be particularly useful for women entering menopause as vaginal pH generally rises due to the decreased amount of estrogen being produced. The firmware can detect these trends and notify the user via the LCD 330 that a noticeable change has occurred and that a visit with a physician may be required.

As also mentioned above, when using the device to monitor fertility status, the device 100 will be used to take the pH and temperature measurements at the ectocervix area. For monitoring fertility a daily measurement cycle will be taken for at least one but preferably several female mammalian fertility cycles. In the human female, this cycle is typically 28 days. The fertility cycle for a typical women is generally during a 3 day window on days 11-14 of the 28 day cycle. However in women who are having a difficult time conceiving this could be very narrow window (i.e. a window of just hours) or this window could be skewed from the normal cycle (i.e. days 17-18). In the case of a very narrow window multiple readings may need to be taken with in a short period of time to provide optimal timing. After enough data has been stored in the memory within the handle 300, the firmware can then analyze the stored pH, temperature and date/time stamp to determine the ovulation profile of the user. Any new data then measured can be compared against this profile to determine that an ovulation cycle is eminent or present. The data from the logic unit memory could be displayed as an output signal as a graphical indicia on the LCD 330 to show the ovulation cycle. If a segmented LCD display 330 is used, a simple indication that ovulation is imminent or in process would be displayed. This could be a flashing display or an ovulation icon. The stored data can also be downloaded to an external device like a PC. This download function is accomplished by the user selecting the proper control button 340, 341 and 342 functions to initiate this data transfer through external data ports 314 or 315.

Although an exemplary embodiment of the invention has been described in detail above, those skilled in the art will readily appreciate that the embodiment may be modified without departing from the novel advantages of the invention. The invention is not limited to the embodiments disclosed, but it is intended to cover modifications within the spirit and scope of the present invention as defined by the following claims.

What is claimed is:

1. An apparatus for measuring a physiological condition within a mammal comprising:
   a probe for insertion into a body lumen of the mammal, the probe comprising:
   an elongated tubular housing having a first internal cavity;
   a first circuit board located within the first internal cavity;
   a pH sensor for measuring pH within the body lumen located at a distal portion of the elongated tubular housing, the pH sensor generating a pH signal indicative of the measured pH and operably coupled to the first circuit board;
   a memory device storing parametric data unique to the pH sensor, the memory device located within the first internal cavity and operably coupled to the first circuit board;
   a temperature sensor for measuring temperature within the body lumen and generating a temperature signal indicative of the measured temperature, the temperature sensor located at the distal portion of the elongated tubular housing and operably coupled to the first circuit board; and
   a first interface connector located at a proximal portion of the elongated tubular housing and operably coupled to the first circuit board;
   a handle for manipulating tile probe, the handle comprising:
   a second housing having a second internal cavity;
   a second circuit board located within the second internal cavity;
   a microprocessor for processing the pH signal and generating an output signal based on the processing of the pH signal, the microprocessor located within the second internal cavity and operably coupled to the second circuit board;
   a display device on the second housing for displaying the output signal generated by the microprocessor and operably coupled to the second circuit board; and
   a second interface connector located at the second housing and operably coupled to the second circuit board;
   the probe connected to the handle in a manner that allows the probe and the handle to be repetitively engaged and disengaged from each other;
   wherein when the probe is connected to the handle, the first and second interface connectors are in electrical connection so that the microprocessor retrieves the parametric data from the memory device of the probe and receives the pH signal;
   wherein the microprocessor processes the temperature signal and generates the output signal based on the processing of the pH signal and the temperature signal; and
   wherein the output signal represents the measured physiological condition and comprises vaginal health, cervical health, and/or fertility status.

2. The apparatus of claim 1 further comprising:
   wherein the first internal cavity is separated into a first internal chamber and a second internal chamber by a transverse wall;
   wherein the first circuit board is located within the first internal chamber and wherein the second chamber is filled with an electrolyte solution buffered at a known pH and hermetically sealed; and
   wherein the probe further comprises a diaphragm located at the distal portion of the elongated tubular housing having a first portion in contact with the electrolyte solution and a second portion exposed to the body lumen.

3. The apparatus of claim 2 further comprising:
   a well formed into the distal portion of the elongated tubular housing;
   the temperature sensor, the pH sensor and the diaphragm located within the well; and
   wherein the probe extends along a longitudinal axis, and wherein the temperature sensor, the pH sensor and the diaphragm are aligned along an axis that is substantially parallel to the longitudinal axis.

4. The apparatus of claim 1 wherein the handle further comprises a power source located within the handle, the power source providing power to the first and second circuit boards when the probe is connected to the handle and wherein the handle further comprises user controls located on the handle and operably coupled to the second circuit board.

5. The apparatus of claim 1 wherein the pH sensor is an ion-sensitive field effect transistor (ISFET) and the parametric data includes first ISFET slope data determined at ambient temperature and second ISFET slope data determined at normal body temperature.

6. The apparatus of claim 5 further comprising:
a socket formed into the second housing, the second interface connector located within the socket; and
wherein when the probe is connected to the handle, the proximal portion of the elongated tubular housing extends into the socket of the handle so that the first and second interface connectors are in electrical connection.

7. The apparatus of claim 1 wherein the body lumen is a vagina and the handle further comprises a second memory device operably coupled to the second circuit board, the second memory device storing algorithms for identifying a fertility period based on cervical pH and temperature.

8. The apparatus of claim 7 wherein the pH sensor is an ion-sensitive field effect transistor (ISFET) and the parametric data includes first ISFET slope data determined at ambient temperature and second ISFET slope data determined at normal body temperature.

9. The apparatus of claim 1 further comprising:
a diaphragm located at the distal portion of the elongated tubular housing;
wherein the temperature sensor is a thermistor covered by a metal cap that is exposed through a first opening in the elongated tubular housing, wherein the pH sensor is exposed through a second opening in the elongated tubular housing, and wherein the diaphragm is exposed through a third opening in the elongated tubular housing; and
wherein the probe extends along a longitudinal axis, and wherein the first, second and third openings in the elongated tubular housing are aligned along an axis that is substantially parallel to the longitudinal axis.

10. The apparatus of claim 9 further comprising:
a space between the thermistor and the metal cap that is filled with a thermally conductive dielectric epoxy; and
wherein a first seal is formed between the metal cap and the elongated tubular housing and a second seal is formed between the pH sensor and the elongated tubular housing so that fluids from the body lumen are unable to reach the second printed circuit board through the first and/or second openings.

11. An apparatus for measuring a physiological condition within a mammal comprising:
an elongated housing extending along a longitudinal axis from a proximal end to a distal end, the housing having an internal cavity;
a transverse wall extending along the longitudinal axis that separates the internal cavity into a first chamber and a second chamber, the first and second chambers isolated from one another and extending in an axially adjacent manner along the longitudinal axis;
a par-cylindrical cutout in the elongated housing forming an open end of the first chamber and exposing a portion of the transverse wall;
a pH sensor for measuring pH within a body lumen of the mammal and a temperature sensor for measuring temperature within the body lumen of the mammal, the pH sensor and the temperature sensor operably coupled to a first circuit board and located on the exposed portion of the transverse wall;
a par-cylindrical cover having a well for collecting biological fluids, the well defined by an annular wall and a floor, and first and second openings forming first and second passageways through the floor of the well respectively;
the par-cylindrical cover secured to the elongated housing so that the pH sensor is exposed via the first opening and the temperature sensor is exposed via the second opening, the par-cylindrical cover covering the par-cylindrical cutout so as to hermetically seal the open end of the first chamber;
a memory device located within the first chamber and operably coupled to tile first circuit board, the memory device storing parametric data unique to the pH sensor;
wherein the pH sensor is an ion-sensitive field effect transistor (ISFET) and the parametric data includes first ISFET slope data determined at ambient temperature and second ISFET slope data determined at normal body temperature;
a second housing comprising a socket, the elongated housing extending from the socket of the second housing, the second housing forming a handle to manipulate the elongated housing:
wherein the second housing houses a microprocessor for receiving and processing signals generated by the pH sensor and the temperature sensor, the microprocessor generating an output signal based on the processing of the signals from the pH sensor and the temperature sensor, and a display device for displaying the output signal generated by the microprocessor, the microprocessor and the display device operably coupled to a second circuit board;
a first interface connector located at a proximal portion of the elongated housing and operably coupled to the first circuit board;
a second interface connector located at the second housing and operably coupled to the second circuit board;
wherein when the elongated housing is connected to and extends from the socket of the second housing, the first and second interface connectors are in electrical connection so that the microprocessor retrieves the parametric data from the memory device and receives the signals generated by the pH sensor and tile temperature sensor; and
wherein the output signal represents the measured physiological condition and comprises vaginal health, cervical health, and/or fertility status.

12. The apparatus of claim 11 wherein a first hermetic seal is formed about a perimeter of the first opening and a second hermetic seal is formed about a perimeter of the second opening.

13. The apparatus of claim 11 further comprising:
an electrolyte solution buffered at a known pH in the second chamber;
a diaphragm extending through an opening in the exposed portion of the transverse wall and into the second chamber in contact with the electrolyte solution, a portion of the diaphragm protruding from the exposed portion of the transverse wall;
wherein the par-cylindrical cover comprises a third opening forming a third passageway through the floor of the well, the diaphragm exposed via the third opening; and
wherein the pH sensor, the temperature sensor and the diaphragm are aligned along an axis that is substantially parallel to the longitudinal axis.

14. The apparatus of claim 11 further comprising:
the first circuit board operably coupling the pH sensor, the temperature sensor, an electrode and a memory device storing parametric data unique to the pH sensor;

the first circuit board mounted to the transverse wall within the first chamber, the electrode extending into the second chamber through a plug that hermetically seals an end of the second chamber; and an electrolyte solution of a known pH filling the second chamber, the electrode immersed in the electrolyte solution.

15. The apparatus of claim 11 further comprising:
wherein the temperature sensor is a thermistor covered by a metal cap that is exposed through the second opening in the par-cylindrical cover, the thermistor and the metal cap being separated by a space that is filled with a thermally conductive dielectric epoxy; and wherein a first seal is formed between the metal cap and the par-cylindrical cover and a second seal is formed between the pH sensor and the par-cylindrical cover so that fluids are unable to reach the second printed circuit board through the first and/or second openings.

16. An apparatus for measuring a physiological condition within a mammal comprising:

an elongated probe for insertion into a body lumen of the mammal, the probe comprising a first circuit board operably coupling an ion-sensitive field effect transistor (ISFET) for measuring pH within the body lumen and generating a pH signal indicative of the measured pH, a temperature sensor for measuring temperature within the body lumen and generating a temperature signal indicative of the measured temperature, a diaphragm in contact with an electrolyte solution buffered at a known pH, a memory device storing ISFET slope data at both ambient temperature and normal body temperature for the ISFET, and a first interface connector, wherein the ISFET, temperature sensor and diaphragm are located at a distal portion of the probe and the first interface connector is located at a proximal portion of the probe;

a handle for manipulating the probe, the handle comprising a second circuit board operably coupling a microprocessor for receiving the pH and temperature signals and generating an output signal based on the processing of the pH and temperature signals and the ISFET slope data, a display device for displaying the output signal generated by the microprocessor, and a second interface connector;

the probe connected to the handle in a manner that allows the probe and the handle to be repetitively engaged and disengaged from each other;

wherein when the probe is connected to the handle, the first and second interface connectors are in electrical connection so that the microprocessor retrieves the ISFET slope data from the memory device of the probe and receives the pH and temperature signals; and wherein the output signal represents the measured physiological condition and comprises vaginal health, cervical health, and/or fertility status.

17. The apparatus of claim 16 further comprising:
wherein the handle further comprises a socket, the second interface connector located within the socket, and wherein when the probe is connected to the handle, the proximal portion of the probe extends into the socket of the handle; and wherein the probe and the handle are connected together by one of a tight-fit engagement, a threaded engagement, and a snap-fit engagement.

18. The apparatus of claim 16 wherein the temperature sensor is a thermistor covered by a metal cap that is exposed through a first opening in a wall of the probe, wherein the ISFET is exposed through a second opening in the wall of the probe, wherein a space between the thermistor and the metal cap is filled with a thermally conductive dielectric epoxy and wherein a first seal is formed between the metal cap and the wall of the probe and a second seal is formed between the ISFET and the wall of the probe so that fluids from the body lumen are unable to reach the second printed circuit board through the first and/or second openings.

* * * * *